US012565481B2

(12) United States Patent
Wang et al.

(10) Patent No.: US 12,565,481 B2
(45) Date of Patent: Mar. 3, 2026

(54) 6,7-DIMETHOXY-3-(PYRIDIN-2-YL)QUINOLINE COMPOUNDS FOR INHIBITING RET

(71) Applicant: Guangzhou Baiyunshan Pharmaceutical Holdings Co., Ltd. Baiyunshan Pharmaceutical General Factory, Guangzhou (CN)

(72) Inventors: Jiansong Wang, Guangzhou (CN); Yang Zhang, Shanghai (CN); Zhibo Luo, Guangzhou (CN); Rongxin Huang, Shanghai (CN); Jikui Sun, Shanghai (CN); Jie Li, Shanghai (CN); Wentao Wu, Shanghai (CN); Jian Li, Shanghai (CN); Shuhui Chen, Shanghai (CN); Yingxia Bao, Guangzhou (CN); Wei Wang, Guangzhou (CN); Zhoufan Xie, Guangzhou (CN)

(73) Assignee: Guangzhou Baiyunshan Pharmaceutical Holdings Co., Ltd. Baiyunshan Pharmaceutical General Factory, Guangzhou (CN)

( * ) Notice: Subject to any disclaimer, the term of this patent is extended or adjusted under 35 U.S.C. 154(b) by 832 days.

(21) Appl. No.: 17/800,609

(22) PCT Filed: Feb. 19, 2021

(86) PCT No.: PCT/CN2021/076918
§ 371 (c)(1),
(2) Date: Aug. 18, 2022

(87) PCT Pub. No.: WO2021/164742
PCT Pub. Date: Aug. 26, 2021

(65) Prior Publication Data

US 2023/0312504 A1 Oct. 5, 2023

(30) Foreign Application Priority Data

Feb. 20, 2020 (CN) ......................... 202010106990.2
Jan. 13, 2021 (CN) ......................... 202110065553.5

(51) Int. Cl.
*C07D 401/04* (2006.01)
*C07D 405/14* (2006.01)
*C07D 471/08* (2006.01)

(52) U.S. Cl.
CPC ......... *C07D 401/04* (2013.01); *C07D 405/14* (2013.01); *C07D 471/08* (2013.01)

(58) Field of Classification Search
None
See application file for complete search history.

(56) References Cited

U.S. PATENT DOCUMENTS

2020/0039974 A1* 2/2020 Inagaki ................ C07D 413/14

FOREIGN PATENT DOCUMENTS

| | | | | |
|---|---|---|---|---|
| CN | 102036963 A | | 4/2011 | |
| CN | 105683182 A | | 6/2016 | |
| CN | 109195972 A | | 1/2019 | |
| CN | 109761899 A | | 5/2019 | |
| CN | 110036007 A | | 7/2019 | |
| JP | 2016516026 A | | 6/2016 | |
| WO | 2006/057922 A2 | | 6/2006 | |
| WO | 2010/101849 A1 | | 9/2010 | |
| WO | 2015/031613 A1 | | 3/2015 | |
| WO | 2016/119017 A1 | | 8/2016 | |
| WO | 2017/145050 A1 | | 8/2017 | |
| WO | 2017/152117 A1 | | 9/2017 | |
| WO | WO-2018060714 A1 | * | 4/2018 | A61P 43/00 |
| WO | WO-2021164741 A1 | * | 8/2021 | A61P 35/00 |

OTHER PUBLICATIONS

Pasini et al. "RET mutations in human disease" Trends in Genetics, 1996, 12, 4, 138-144. DOI: 10.1016/0168-9525(96)10012-3 (Year: 1996).*
The State Intellectual Property Office of People's Republic of China,First Office Action for Chinese Application No. 202180015245.X and English translation, mailed Jun. 9, 2023, pp. 1-12.
The State Intellectual Property Office of People's Republic of China,First search for Chinese Application No. 202180015245.X and English translation, mailed Jun. 5, 2023, pp. 1-6.
Decision to Grant a Patent Japanese Application No. 2022-547767 and English translation, pp. 1-5.

(Continued)

*Primary Examiner* — Jennifer A Berrios
*Assistant Examiner* — Sophia Reilly
(74) *Attorney, Agent, or Firm* — Hoffmann & Baron LLP

(57) ABSTRACT

Disclosed are a class of compounds represented by formula (II), and isomers or pharmaceutically acceptable salts thereof.

(II)

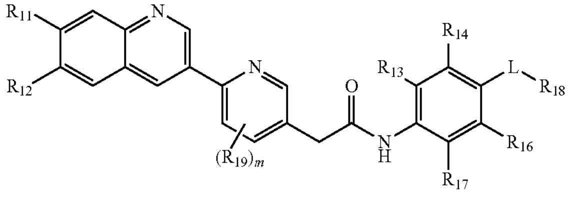

18 Claims, No Drawings

(56) References Cited

OTHER PUBLICATIONS

Notice of Reasons for Refusal Japanese Application No. 2022-547767 and English translation, pp. 1-6.
Search Report by Registered Search Organization Japanese Application No. 2022-547767 and English translation, pp. 1-34.
European Search Opinion for European Application No. EP21756247, pp. 1-2.
Supplementary European Search Report for European Application No. EP21756247, mailed Jun. 14, 2023, pp. 1-3.
R. B Silverman, Richard B. The Organic Chemistry of Drug Design and Drug Action [M]. Chemical industry press,2008.
Schenck Eidam et al., Discovery of a first in-Class Gut-Restricted RET Kinase Inhibitor as a Clinical Candidate for the Treatment of IBS, ACS Medicinal Chemistry Letters,2018, 9 (7), 623-628.

* cited by examiner

6,7-DIMETHOXY-3-(PYRIDIN-2-YL)QUINOLINE COMPOUNDS FOR INHIBITING RET

CROSS-REFERENCE TO RELATED APPLICATIONS

The present application is a national phase entry under 35 USC § 371 of International Application PCT/CN2021/076918, filed on Feb. 19, 2021, which claims the benefit of and priority to Chinese Patent Application No. CN202010106990.2, filed on Feb. 20, 2020, and Chinese Patent Application No. CN202110065553.5, filed on Jan. 13, 2021, the entire disclosures of which are incorporated herein by reference.

TECHNICAL FIELD

The present disclosure relates to a class of compounds represented by formula (II), and isomers or pharmaceutically acceptable salts thereof.

BACKGROUND ART

RET gene is a proto-oncogene that rearranges during transfection, hence the name. The RET gene encodes a cytomembrane receptor tyrosine kinase. When growth factors bind to the extracellular region of RET, a series of chemical chain reactions in cells is triggered, according to the signal received by receptors, which leads to cell division and maturation, and exerts corresponding effects on organ development and tissue homeostasis. RET protein plays an important role in the development of several nerves (including the enteric and autonomic nervous system).

Aberrant activation or mutation of RET kinase has been demonstrated to be responsible for various tumorigenesis, including familial medullary thyroid carcinoma (FMTC), papillary thyroid carcinoma (PTC), multiple endocrine neoplasia (MEN2A and 2B) and non-small cell lung cancer (NSCLC), etc. Selective RET inhibitors, e.g., LOXO-292, BLU-667, and DS-5010, have been demonstrated in clinical trials for the treatment of RET-related tumors.

The present disclosure aims to develop a class of quinoline derivatives as RET inhibitors for the treatment of tumors or intestinal diseases related to abnormal activation of RET.

SUMMARY

The present disclosure provides a compound of formula (II), or a pharmaceutically acceptable salt thereof, (II)

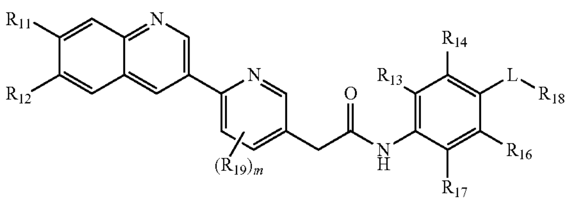

wherein,

L is selected from —$CH_2$—, —$NR_{10}$— and —$CH_2NR_{10}$—;

$R_{10}$ is selected from H and $CH_3$;

$R_{11}$ is —$OCH_3$;

$R_{12}$ is —$OCH_3$;

$R_{13}$ is selected from H, F, Cl, Br, I, OH, $NH_2$, CN and $CH_3$;

$R_{14}$ is selected from H, F, Cl, Br, I, OH, $NH_2$, CN and $C_{1-3}$ alkyl, wherein the $C_{1-3}$ alkyl is optionally substituted by one, two or three $R_{1d}$;

$R_{16}$ is selected from H, F, Cl, Br, I, OH, $NH_2$, CN and $C_{1-3}$ alkyl, wherein the $C_{1-3}$ alkyl is optionally substituted by one, two or three $R_{1g}$;

$R_{17}$ is selected from H, F, Cl, Br, I, OH, $NH_2$, CN and $CH_3$;

$R_{18}$ is selected from 3,6-diazabicyclo-[3.3.1]heptanyl, piperazinyl, piperidinyl and $C_{1-6}$ alkyl, wherein the 3,6-diazabicyclo-[3.3.1]heptanyl, the piperazinyl, the piperidinyl and the $C_{1-6}$ alkyl are optionally substituted by one, two or three $R_{1h}$;

each $R_{19}$ is independently selected from H, F, Cl, Br, I and $CH_3$, respectively;

m is selected from 0, 1, 2 and 3;

$R_{1d}$ and $R_{1g}$ are independently selected from H, F, Cl, Br, I, OH, $NH_2$, CN and $CH_3$, respectively;

$R_{1h}$ is independently selected from H, F, Cl, Br, I, OH, $NH_2$, CN,

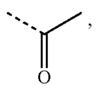

$C_{1-3}$ alkyl, $C_{1-3}$ alkylamino and oxetanyl, respectively, wherein the

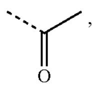

the $C_{1-3}$ alkyl, the $C_{1-3}$ alkylamino and the oxetanyl are optionally substituted by one, two or three R; each R is independently selected from H, F, Cl and I, respectively.

In some embodiments of the present disclosure, the compound or the pharmaceutically acceptable salt thereof, wherein, $R_{13}$ is selected from H and F, and other variables are as defined in the present disclosure.

In some embodiments of the present disclosure, the compound or the pharmaceutically acceptable salt thereof, wherein, $R_{14}$ is selected from H and $CF_3$, and other variables are as defined in the present disclosure.

In some embodiments of the present disclosure, the compound or the pharmaceutically acceptable salt thereof, wherein, $R_{16}$ is $CF_3$, and other variables are as defined in the present disclosure.

In some embodiments of the present disclosure, the compound or the pharmaceutically acceptable salt thereof, wherein, $R_{17}$ is H, and other variables are as defined in the present disclosure.

In some embodiments of the present disclosure, the compound or the pharmaceutically acceptable salt thereof, wherein, Rin is selected from

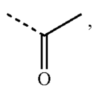

$CH_3$, $CH_2CH_3$,

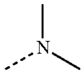
and
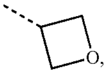

wherein the

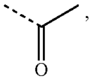

the $CH_3$, the $CH_2CH_3$, the

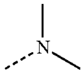

and the

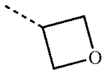

are optionally substituted by one, two or three R, and other variables are as defined in the present disclosure.

In some embodiments of the present disclosure, the compound or the pharmaceutically acceptable salt thereof, wherein, $R_{1h}$ is selected from

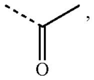

$CH_3$, $CH_2CH_3$, $CH_2CF_3$,

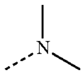
and
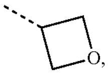

and, and other variables are as defined in the present disclosure.

In some embodiments of the present disclosure, the compound or the pharmaceutically acceptable salt thereof, wherein, $R_{18}$ is selected from $CH_2CH_3$,

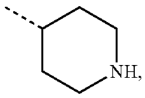
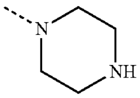
and
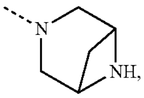

wherein the $CH_2CH_3$, the

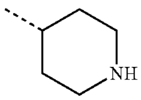
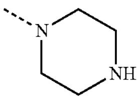
and the
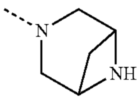

are optionally substituted by one, two or three $R_{1h}$, and other variables are as defined in the present disclosure.

In some embodiments of the present disclosure, the compound or the pharmaceutically acceptable salt thereof, wherein, $R_{18}$ is selected from

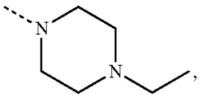
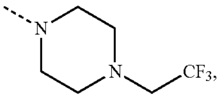
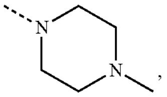
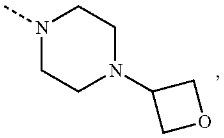
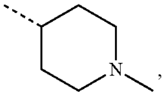
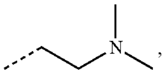
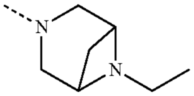
and
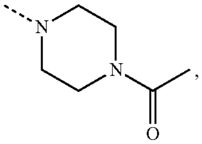

and other variables are as defined in the present disclosure.

In some embodiments of the present disclosure, the compound or the pharmaceutically acceptable salt thereof, wherein, the structural unit

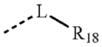

is selected from

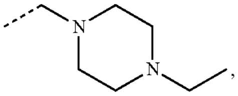
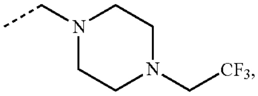
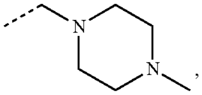
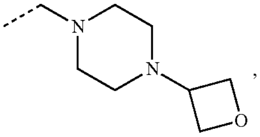
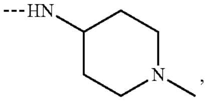
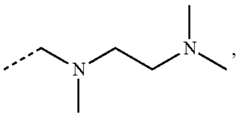
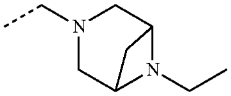
and
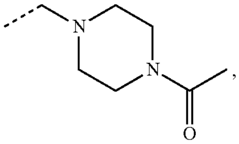

and other variables are as defined in the present disclosure.

The present disclosure provides a compound of formula (II), or a pharmaceutically acceptable salt thereof, (II)

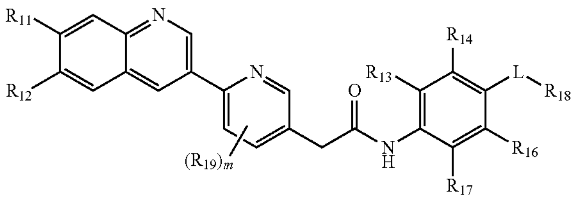

wherein,

L is selected from —$CH_2$—, —$NR_{10}$— and —$CH_2NR_{10}$—;

$R_{10}$ is selected from H and $CH_3$;

$R_{11}$ is —$OCH_3$;

$R_{12}$ is —$OCH_3$;

$R_{13}$ is selected from H, F, Cl, Br, I, OH, $NH_2$, CN and $CH_3$;

$R_{14}$ is selected from H, F, Cl, Br, I, OH, $NH_2$, CN and $C_{1-3}$ alkyl, wherein the $C_{1-3}$ alkyl is optionally substituted by one, two or three $R_{1d}$;

$R_{16}$ is selected from H, F, Cl, Br, I, OH, $NH_2$, CN and $C_{1-3}$ alkyl, wherein the $C_{1-3}$ alkyl is optionally substituted by one, two or three $R_{18}$;

$R_{17}$ is selected from H, F, Cl, Br, I, OH, $NH_2$, CN and $CH_3$;

$R_{18}$ is selected from piperazinyl, piperidinyl and $C_{1-6}$ alkyl, wherein the piperazinyl, the piperidinyl and the $C_{1-6}$ alkyl are optionally substituted by one, two or three $R_{1h}$;

each $R_{19}$ is independently selected from H, F, Cl, Br, I and $CH_3$, respectively;

$R_{10}$ is selected from H and $CH_3$;

m is selected from 0, 1, 2 and 3;

$R_{1d}$ and $R_{1g}$ are independently selected from H, F, Cl, Br, I, OH, $NH_2$, CN and $CH_3$, respectively;

$R_{1h}$ is independently selected from H, F, Cl, Br, I, OH, $NH_2$, CN, $C_{1-3}$ alkyl, $C_{1-3}$ alkylamino and oxetanyl, wherein the $C_{1-3}$ alkyl, the $C_{1-3}$ alkylamino and the oxetanyl are optionally substituted by one, two or three R;

each R is independently selected from H, F, Cl and I, respectively.

In some embodiments of the present disclosure, the compound or the pharmaceutically acceptable salt thereof, wherein, $R_{13}$ is selected from H and F, and other variables are as defined in the present disclosure.

In some embodiments of the present disclosure, the compound or the pharmaceutically acceptable salt thereof, wherein, $R_{14}$ is selected from H and $CF_3$, and other variables are as defined in the present disclosure.

In some embodiments of the present disclosure, the compound or the pharmaceutically acceptable salt thereof, wherein, $R_{16}$ is $CF_3$, and other variables are as defined in the present disclosure.

In some embodiments of the present disclosure, the compound or the pharmaceutically acceptable salt thereof, wherein, $R_{17}$ is H, and other variables are as defined in the present disclosure.

In some embodiments of the present disclosure, the compound or the pharmaceutically acceptable salt thereof, wherein, $R_{1h}$ is selected from $CH_3$, $CH_2CH_3$,

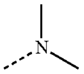

and

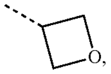

wherein the $CH_3$, the $CH_2CH_3$, the

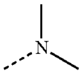

and the

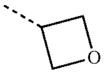

are optionally substituted by one, two or three R, and other variables are as defined in the present disclosure.

In some embodiments of the present disclosure, the compound or the pharmaceutically acceptable salt thereof, wherein, $R_{1h}$ is selected from $CH_3$, $CH_2CH_3$, $CH_2CF_3$,

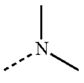

and

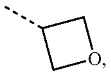

and other variables are as defined in the present disclosure.

In some embodiments of the present disclosure, the compound or the pharmaceutically acceptable salt thereof, wherein, Rix is selected from $CH_2CH_3$,

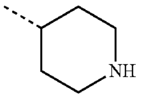

and

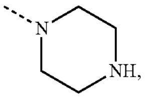

wherein the $CH_2CH_3$,

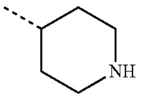

and

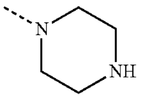

are optionally substituted by one, two or three $R_{1h}$, and other variables are as defined in the present disclosure.

In some embodiments of the present disclosure, the compound or the pharmaceutically acceptable salt thereof, wherein, Rim is selected from

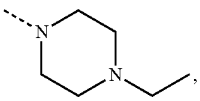

,

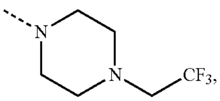

,

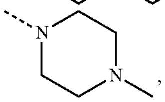

,

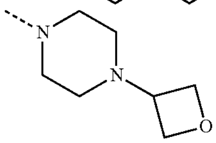

,

-continued

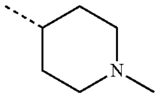,
and
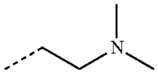, and other variables are as defined in the present disclosure.

In some embodiments of the present disclosure, the compound or the pharmaceutically acceptable salt thereof, wherein, the structural unit

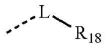

is selected from

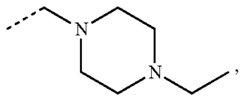,
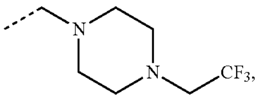,

-continued

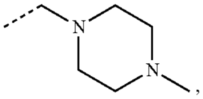,
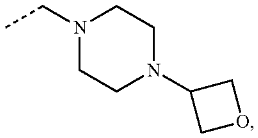,
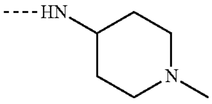
and
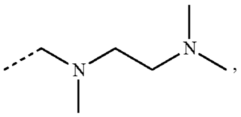, and other variables are as defined in the present disclosure.

In some embodiments of the present disclosure, the compound or the pharmaceutically acceptable salt thereof, (II-1)

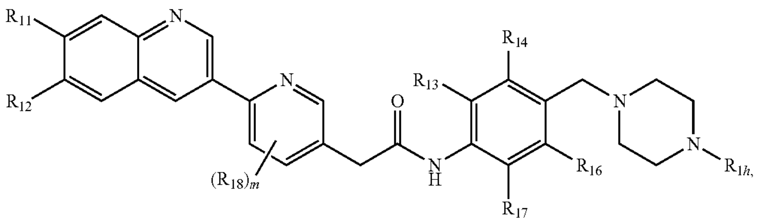

(II-2)

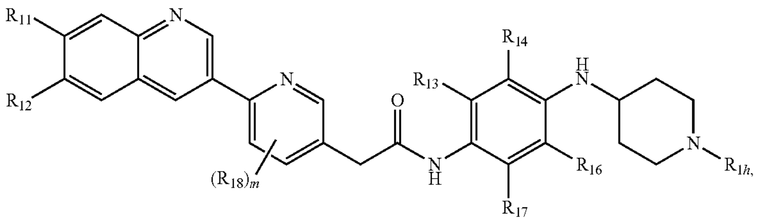

(II-3)

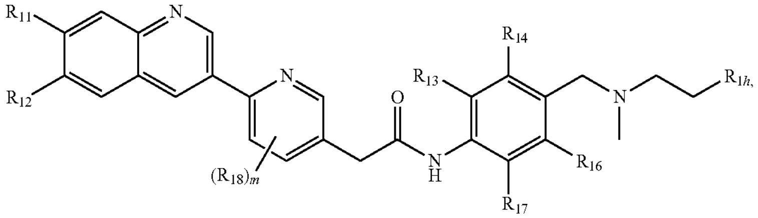

and (P-1)

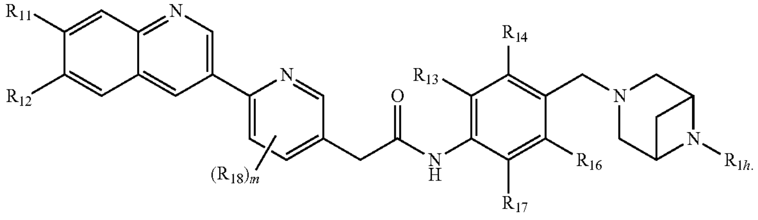

wherein, Ru, $R_{12}$, $R_{13}$, $R_{14}$, $R_{16}$, $R_{17}$, $R_{19}$, $R_{1h}$ and m are as defined in the present disclosure.

Other embodiments of the present disclosure can be obtained by the arbitrary combination of the above variables.
The present disclosure also provides compounds as shown below, or pharmaceutically acceptable salts thereof,
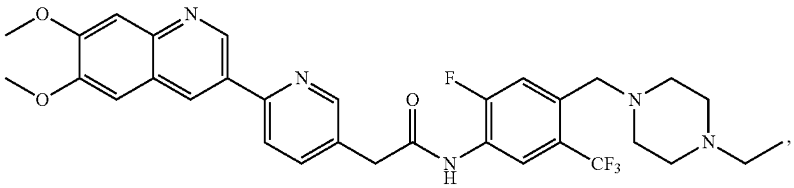
,
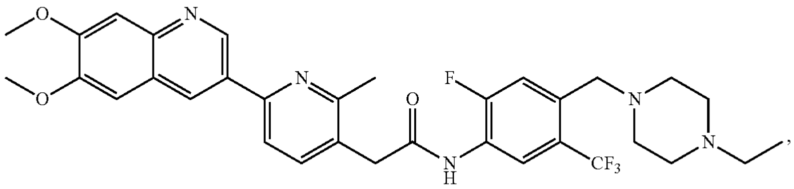
,
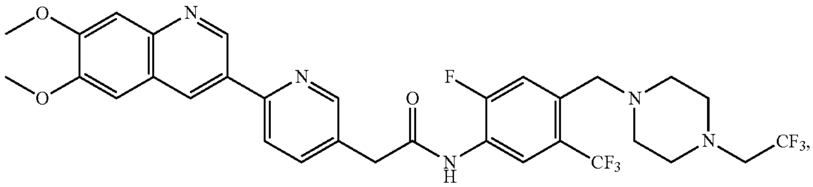
,
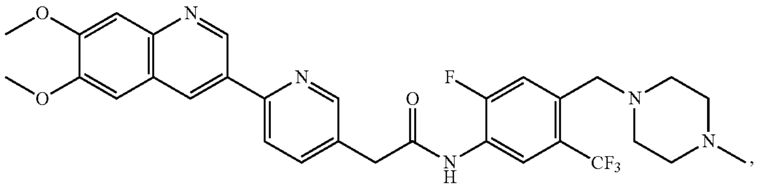
,
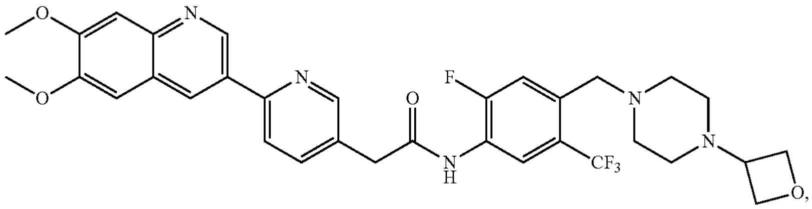
,
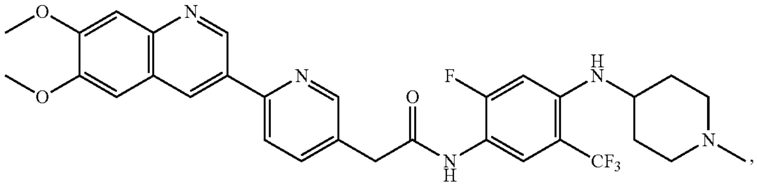
,
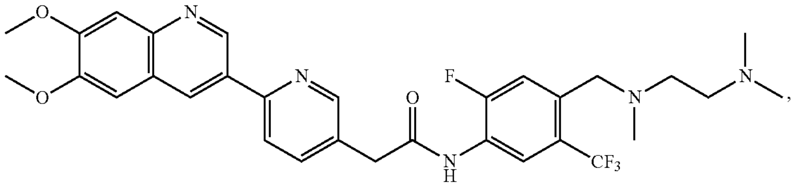
,
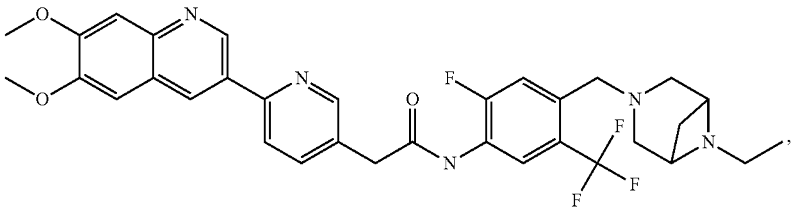
, -continued

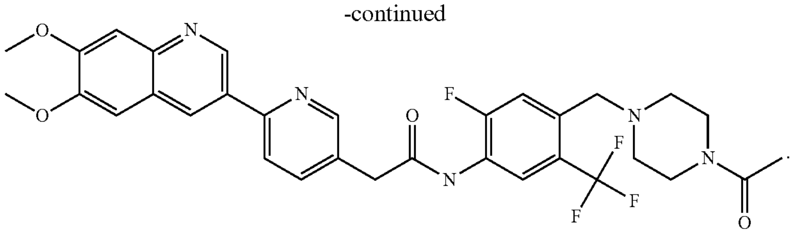

The present disclosure also provides a pharmaceutical composition comprising a therapeutically effective amount of the compound or the pharmaceutically acceptable salt thereof as the active ingredient, and a pharmaceutically acceptable carrier.

The present disclosure also provides a use of the compound, or the pharmaceutically acceptable salt thereof, or the pharmaceutical composition in the preparation of a medicament for treating RET-related disease.

TECHNICAL EFFECTS

The compounds of the present disclosure possess an excellent inhibitory effect on both wild-type and V804M mutant RET kinases, have excellent properties in terms of Phase I metabolic stability, safety of drug interaction. Pharmacokinetic studies demonstrate superior oral absorption and high bioavailability of the compounds.

Definitions and Descriptions

Unless otherwise specified, the following terms and phrases used herein are intended to have the following meanings. A particular term or phrase should not be considered uncertain or unclear without a specific definition, but should be understood in the ordinary sense. When a commodity name appears in this article, it is intended to refer to the corresponding commodity or its active ingredients.

The term "pharmaceutically acceptable" refers to compounds, materials, compositions and/or formulations that are within a range of reliable medical judgment and are suitable for contact with the tissues of human beings and animals without excessive toxicity, irritation, allergic response or other problems or complications, which are compatible with reasonable benefits/risks.

The term "pharmaceutically acceptable salts" refers to the salts of the compounds of the present disclosure, which are prepared from the compounds with specific substituents found by the present disclosure and relatively non-toxic acids or bases.

When the compounds of the present disclosure contain relatively acidic functional groups, basic addition salts can be obtained by contacting such compounds with sufficient bases in pure solutions or appropriate inert solvents. Pharmaceutically acceptable basic addition salts include sodium salts, potassium salts, calcium salts, ammonium salts, organic ammonium salts, magnesium salts or the like. When the compounds of the present disclosure contain relatively basic functional groups, acid addition salts can be obtained by contacting such compounds with sufficient acids in pure solutions or appropriate inert solvents. Examples of pharmaceutically acceptable acid addition salts include inorganic acid salts, in which the inorganic acids include hydrochloric acid, hydrobromic acid, nitric acid, carbonic acid, bicarbonate, phosphoric acid, monohydrogen phosphate, dihydrogen phosphate, sulfuric acid, bisulfate, hydroiodic acid, phosphorous acid, etc.; and organic acid salts, in which the organic acids include acetic acid, propanoic acid, isobutyric acid, maleic acid, propanedioic acid, benzoic acid, succinic acid, octanedioic acid, fumaric acid, lactic acid, mandelic acid, phthalic acid, benzenesulfonic acid, p-toluenesulfonic acid, citric acid, tartaric acid, methanesulfonic acid, or the like; amino acid (such as arginine) salts and salts of organic acid such as glucuronic acid are also included. Certain specific compounds of the present disclosure contain basic and acidic functional groups, which can be converted into any base or acid addition salt.

The pharmaceutically acceptable salts of the present disclosure can be synthesized by conventional chemical methods from the parent compounds containing acidic or basic functional groups. Generally, the preparation method of such salts is: in water, organic solvents, or the mixtures of both, the salts are prepared by reacting these compounds in the form of free acids or bases with stoichiometric appropriate bases or acids.

The compounds of the present disclosure can exist in specific geometric or stereoisomeric forms. All of such compounds are conceived in the present disclosure, including cis- and trans-isomers, (−)- and (+)-enantiomers, (R)- and (S)-enantiomers, diastereomers, (D)-isomers, (L)-isomers, the racemic mixtures thereof, and other mixtures, such as enantiomers or non-enantiomerically enriched mixtures, all falling within the scope of the present disclosure. Additional asymmetric carbon atoms may be present in a substituent such as an alkyl group. All such isomers and their mixtures are included within the scope of the present disclosure.

Unless otherwise specified, the term "enantomers" or "optical isomers" refers to stereoisomers that are mirror images of each other.

Unless otherwise specified, the term "cis-trans isomer" or "geometric isomer" is caused by the fact that the double bond or single bond of the carbon atom on the ring cannot rotate freely.

Unless otherwise specified, the term "diastereomer" refers to stereoisomers in which the molecules have two or more chiral centers and are not mirror images of each other.

Unless otherwise specified, "(+)" stands for dextrorotation, "(−)" stands for levorotation, "(f)" stands for racemization.

Unless otherwise specified, the absolute configuration of a stereogenic center is represented by a wedged solid bond ()

and a wedged dashed bond (),

, the relative configuration of a stereogenic center is represented by a straight solid bond ()

and a straight dashed bond ()

, a wave line ()

represents a wedged solid bond ()

or a wedged dashed bond (),

, or a wave line ()

represents a straight solid bond ()

or a straight dashed bond ().

.

Unless otherwise specified, when a double bond structure exists in a compound, such as carbon-carbon double bond, carbon-nitrogen double bond, and nitrogen-nitrogen double bond, and each atom on the double bond is connected with two different substituents (in the double bond containing a nitrogen atom, a pair of lone electrons on the nitrogen atom is regarded as a substituent to which it is connected), if an atom on a double bond in the compound is connected with a wavy line ()

to its substituent, it indicates the (Z) isomer, (E) isomer, or a mixture of the two isomers of the compound.

For example, formula (A) indicates that the compound is in the form of a single isomer of formula (A-1) or formula (A-2), or a mixture of two isomers of formula (A-1) and formula (A-2); formula (B) indicates that the compound is in the form of a single isomer of formula (B-1) or formula (B-2), or a mixture of two isomers of formula (B-1) and formula (B-2). Formula (C) indicates that the compound is in the form of a single isomer of formula (C-1) or formula (C-2), or a mixture of two isomers of formula (C-1) and formula (C-2).

(A)

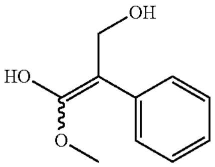

(A-1)

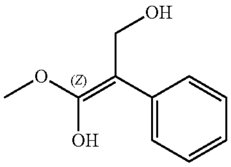

(A-2)

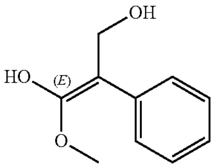

(B)

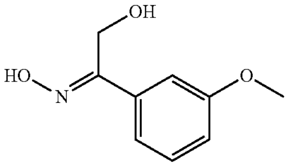

(B-1)

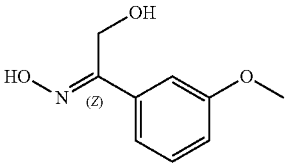

(B-2)

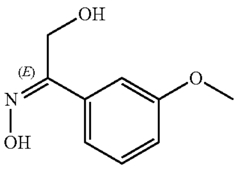

(C)

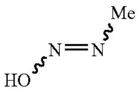

(C-1)

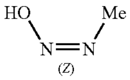

-continued (C-2)

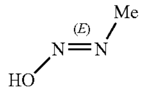

Unless otherwise specified, the term "tautomer" or "tautomeric form" refers to the fact that the different functional isomers are in dynamic equilibrium at room temperature and can be rapidly converted into each other. If tautomers are possible (such as in a solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation through recombination of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched". "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomers, D and L isomers can be prepared by chiral synthesis or chiral reagents or other conventional techniques. If an enantiomer of a compound of the present disclosure is to be obtained, it can be prepared by asymmetric synthesis or by derivatization with chiral auxiliaries, in which the resulting non-enantiomeric mixture is separated and the auxiliary groups are split to provide the pure enantiomers needed. Alternatively, when the molecules contain basic functional groups (such as amino groups) or acidic functional groups (such as carboxyl groups), the non-enantiomeric salts are formed with appropriate optically active acids or bases, then the non-enantiomers are separated by conventional methods known in the art, and the pure enantiomers are recovered. In addition, the separation of the enantiomers and non-enantiomers is usually accomplished by chromatographic methods, which use chiral stationary phases, and are optionally combined with chemical derivatization (e.g., the formation of carbamates from amines).

The compounds of the present disclosure may contain atomic isotopes in non-natural proportions on one or more atoms constituting the compounds. For example, the compounds can be labeled with radioisotopes, such as tritium ($^{3}H$), iodine-125 ($^{125}I$) or C-14 ($^{14}C$). For another example, hydrogen can be replaced by heavy hydrogen to form a deuterated drug, and the bond composed of deuterium and carbon is stronger than the bond composed of common hydrogen and carbon. Compared with undeuterated drugs, deuterated drugs have reduced side effects and increased drug stability, enhanced efficacy and prolonged biological half-life of the drug. All isotopic variations of the compound of the present disclosure, whether radioactive or not, are encompassed within the scope of the present disclosure.

"Optional" or "optionally" means that the subsequent event or condition may occur but not requisite, that the term includes the instance in which the event or condition occurs and the instance in which the event or condition does not occur.

The term "substituted" refers to any one or more hydrogen atoms on a designated atom is replaced with a substituent, which may include heavy hydrogen and variants of hydrogen, as long as the valence state of the specific atom is normal and the substituted compound is stable. When the substituent is a ketone group (i.e., =O), it means that two hydrogen atoms are substituted. The ketone substitution does not occur on an aromatic group. The term "optionally substituted" means that it may or may not be substituted, unless otherwise specified, the type and number of substituents may be arbitrary on the basis of chemical accessibility.

When any variable (e.g., R) occurs more than once in the composition or structure of a compound, its definition at each occurrence is independent. Thus, for example, if a group is substituted with 0-2 R, the group can be substituted optionally with at most two R, and R has a independent option at each occurrence. Furthermore, combinations of substituents and/or their variables are permissible only if such combinations result in stable compounds.

When the number of bonding groups is zero, such as $-(CRR)_0-$, it means that the bonding groups are single bonds.

When one of the variables is selected from single bond, it means that the two groups are linked directly. For example, when L in A-L-Z presents a single bond, it indicates that the structure is actually A-Z.

When a substituent is absent, it means that the substituent does not exist. For example, when X is absent in A-X, it means that the structure is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

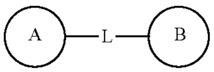

is -M-W—, then -M-W— can link ring A and ring B to form

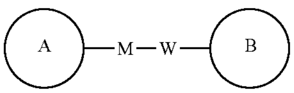

in the direction same as left-to-right reading order, and form

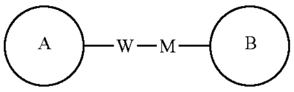

in the direction contrary to left-to-right reading order. A combination of linking groups, substituents and/or variants thereof is allowed only when such combination can result in a stable compound.

Unless otherwise specified, when a group has one or more linkable sites, any one or more sites of the group can be connected to other groups through chemical bonds.

When H atoms are present at a connectable site and there is no designated connecting mode for a chemical bond, the number of the H atoms at the connectable site is correspondingly reduced based on the number of the connected chemical bonds, and a group with a corresponding valence number is thus formed. The chemical bond between the site and other groups can be represented by a straight solid bond (), a straight dashed bond () or a wavy line (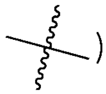).

. For example, the straight solid bond in $—OCH_3$ represents that the group is connected to other group through an oxygen atom; the straight dashed bond in

represents that it is connected to other groups through the two ends of the nitrogen atom in the group. The wavy line in

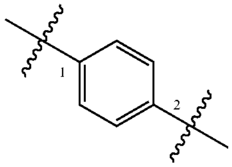 [SMILES: *c1ccc(*)cc1]

represents that the phenyl group is connected to other groups through 1- and 2-position carbon atoms;

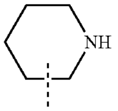

represents that any linkable site on the piperidinyl can be connected to other groups through one chemical bond, including at least four connection ways

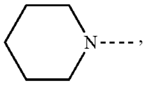 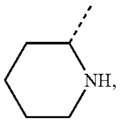 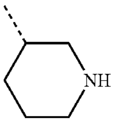 and

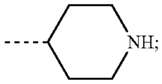

even if a H atom is drawn on —N—,

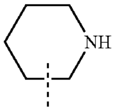

still comprises the group in the connection way of

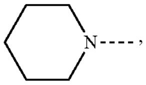

but when one chemical bond is linked, the H at the site will be reduced by one and a corresponding monovalent piperidinyl is formed.

Unless otherwise specified, the term "$C_{1-6}$ alkyl" is used to represent a linear or branched saturated hydrocarbon group composed of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, $C_5$ alkyl, and so on. The $C_{1-6}$ alkyl may be monovalent (such as methyl), divalent (such as methylene) or multivalent (such as methine). Examples of the $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl), hexyl, and the like.

Unless otherwise specified, the term "C-3 alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkylamino" represents an alkyl group which is connected to the rest of the molecule through an amino group and contains 1 to 3 carbon atoms. The $C_{1-3}$ alkylamino includes $C_{1-2}$ alkylamino, $C_3$ alkylamino, $C_2$ alkylamino and so on. Examples of the $C_{1-3}$ alkylamino include, but are not limited to, $—NHCH_3$, $—N(CH_3)_2$, $—NHCH_2CH_3$, $—N(CH_3)CH_2CH_3$, $—NHCH_2CH_2CH_3$, $—NHCH_2(CH_3)_2$, and the like.

The compound of the present disclosure can be prepared by a variety of synthetic methods well known to the skilled in the art, including the following enumerative embodiment, the embodiment formed by combining the following enumerative embodiment with other chemical synthesis methods, and the equivalent replacement well known to the skilled in the art. The preferred embodiment includes, but is not limited to the embodiment of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and φ/ω scan as the scanning mode, and after collecting the relevant data, the crystal structure can be further analyzed by direct method (Shelxs97).

Compounds are named according to conventional naming principles in the field or by ChemDraw®: software, the commercially available compounds use their vendor directory names.

DETAILED DESCRIPTION

The following examples further illustrate the present disclosure, but the present disclosure is not limited thereto. The present disclosure has been described in detail in the text, and its specific embodiments have also been disclosed, for one skilled in the art, it is obvious to modify and improve the embodiments of the present disclosure without departing from the spirit and scope of the present disclosure.

Example 1

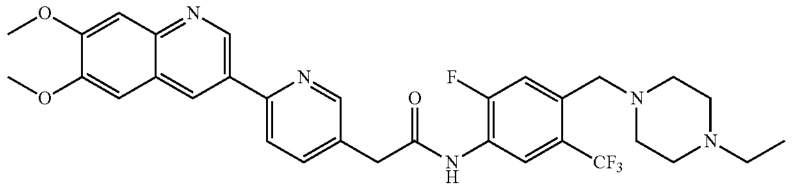

1

Synthetic Route

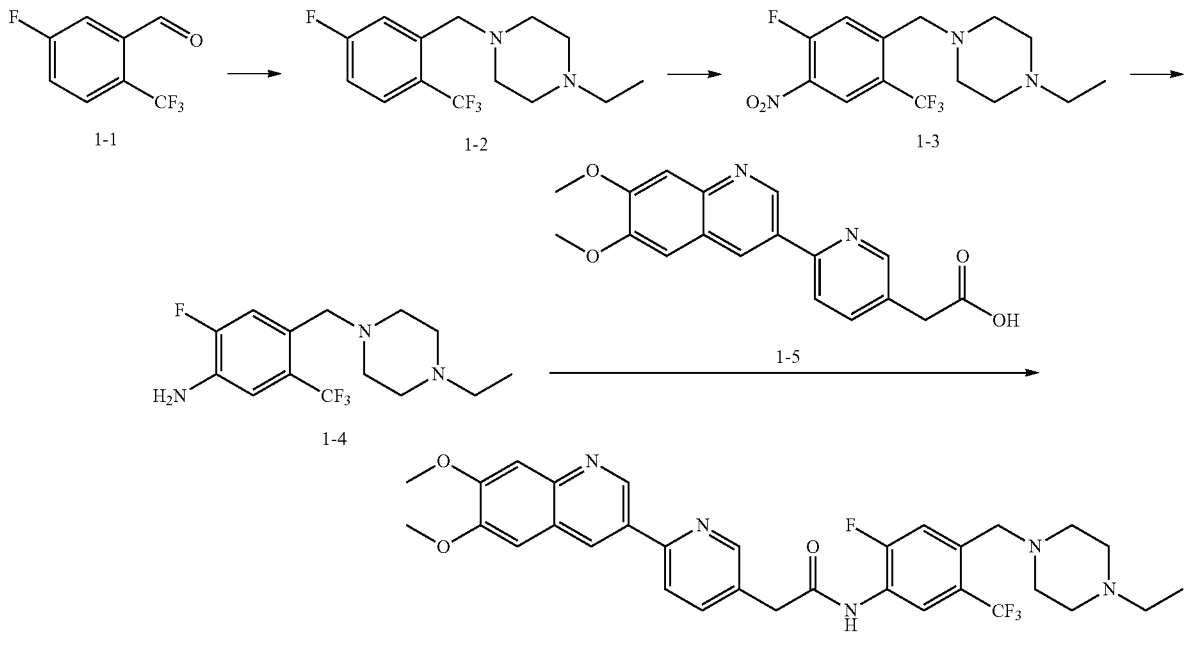

1-1, 1-2, 1-3, 1-5, 1-4, 1

Step 1: Synthesis of Compound 1-2

Compound 1-1 (5 g, 26.03 mmol) and N-ethylpiperazine (4.46 g, 39.04 mmol, 4.96 mL) were added to anhydrous dichloromethane (100.0 mL), the reaction mixture was stirred for 2 hours. Sodium acetate borohydride (16.55 g, 78.08 mmol) was added, and the reaction was stirred at 20° C. for 1 hour. The reaction solution was poured into an aqueous saturated solution of sodium bicarbonate, the pH was adjusted to pH 8, followed by extraction, and the aqueous phase was continued to be extracted with 80 mL of dichloromethane. The organic layers were combined, dried over anhydrous sodium sulfate, filtered and concentrated, The crude product was purified by column passing machine ($CH_2Cl_2$/MeOH: 100:0-20:1) to obtain the corresponding compound 1-2. $^1H$ NMR (400 MHz, $CDCl_3$) δ=7.67-7.53 (m, 2H), 7.03-6.91 (m, 1H), 3.84 (s, 2H), 2.67-2.22 (m, 10H), 1.08 (t, J=7.2 Hz, 3H); MS m/r=291.1[M+H]$^+$.

Step 2: Synthesis of Compound 1-3

Compound 1-2 (10 g, 34.45 mmol) was added into sulfuric acid (37.92 g, 378.92 mmol, 20.61 mL, 98% purity), then mixed with nitric acid (2.44 g, 37.89 mmol, 1.74 mL, 98% purity). The reaction was conducted at 20° C. for 16 hours, and at 50° C. for 6.5 hours. The reaction liquid was added into an aqueous saturated solution of sodium bicarbonate and adjusted to pH 8, and then extracted with ethyl acetate (150 mL×3). The organic layers were combined, washed with an aqueous saturated solution of sodium chloride (300 mL), dried over anhydrous sodium sulfate, filtered and concentrated, to obtain the corresponding compound 1-3. $^1$H NMR (400 MHz, $CDCl_3$) δ=8.39 (d, J=6.8 Hz, 1H), 7.77 (d, J=11.6 Hz, 1H), 3.85 (s, 2H), 3.36-2.42 (m, 10H), 1.49 (t, J=7.2 Hz, 3H).

Step 3: Synthesis of Compound 1-4

Compound 1-3 (3.5 g, 10.44 mmol) was added into methanol (150.0 mL), Raney nickel (4.47 g, 52.19 mmol) was added, and the reaction was conducted at 20° C. for 1 hour in the presence of hydrogen (15 psi). After filtering through a celite plug and concentrating, the crude product was purified by column passing machine ($CH_2Cl_2$/MeOH: 100:0-15:1) to obtain the corresponding compound 1-4. $^1$H NMR (400 MHz, $d_4$-MeOH) δ=7.35 (d, J=12.4 Hz, 1H), 7.15 (d, J=8.4 Hz, 1H), 3.63 (s, 2H), 3.38-3.35 (m, 2H), 3.31-3.07 (m, 5H), 2.90-2.62 (m, 3H), 1.36 (t, J=7.6 Hz, 3H).

Step 4: Synthesis of Compound 1

Compound 1-5 (0.1 g, 308.33 μmol) and compound 1-4 (103.55 mg, 339.16 μmol) were added into pyridine (5.0 mL), T3P (981.04 mg, 1.54 mmol, 916.86 μL, 50% purity) was added dropwisely, the reaction was conducted at 20° C. for 1 h. Water (20 mL) was added into the reaction mixture, extracted with ethyl acetate (15 mL×2). The organic layers were combined, washed with an aqueous saturated solution of sodium chloride (20 mL), dried over anhydrous sodium sulfate, filtered and concentrated, the crude material was purified by HPLC (column: Phenomenex Luna C18, 150×30 mm×5 μm; mobile phase: [$H_2O$ (0.05% HCl)-ACN]acetonitrile %: 10%-45%, 12 min) to obtain compound 1. $^1$H NMR (400 MHz, $d_4$-MeOH) δ=9.55 (s, 2H), 8.80 (s, 1H), 8.52-8.42 (m, 1H), 8.27-8.20 (m, 1H), 8.17-8.08 (m, 1H), 7.76 (s, 2H), 7.57-7.50 (m, 1H), 4.16 (s, 3H), 4.11 (s, 3H), 4.01 (s, 2H), 3.95-3.85 (m, 2H), 3.65-3.55 (m, 2H), 3.27-3.16 (m, 6H), 2.80-2.60 (m, 2H), 1.37 (t, J=7.6 Hz, 3H); MS m/z=612.2 [M+H]$^+$.

Example 2

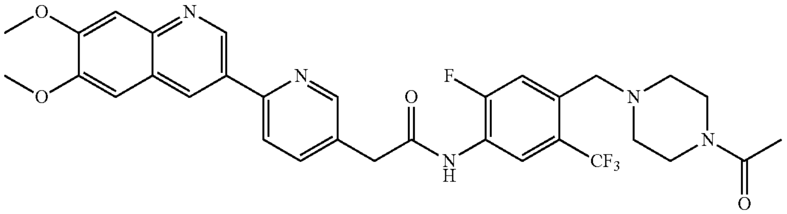

2

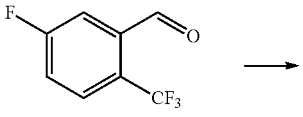

1-1

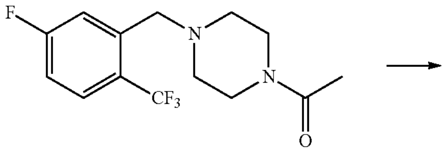

2-2

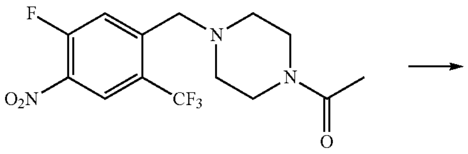

2-3

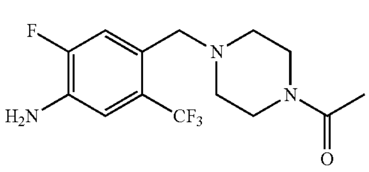

2-4

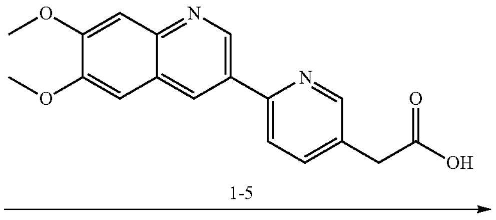

1-5

-continued

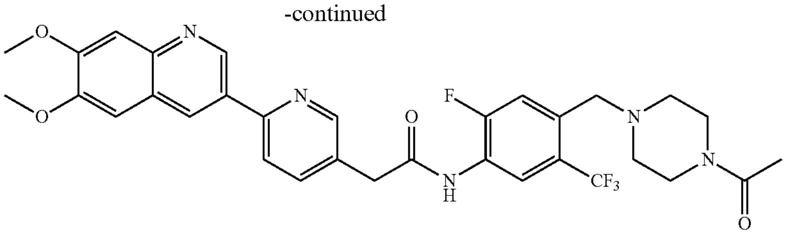

2

Step 1: Synthesis of Compound 2-2

Compound 1-1 (2 g, 10.41 mmol), N-acetylpiperidine (2.00 g, 15.62 mmol), and acetic acid (62.52 mg, 1.04 mmol, 59.54 μL) were added to 1,2-dichloroethane (20 mL), the reaction was conducted at 20° C. for 16 hours under nitrogen atmosphere, then sodium cyanoborohydride (1.31 g, 20.82 mmol) was added, the reaction was conducted at 20° C. for 10 min. An aqueous saturated solution of sodium bicarbonate was added into the reaction solution to adjusted the pH to 8, and then extracted with dichloromethane (20 mL×2). The organic layers were combined, dried over anhydrous sodium sulfate, filtered and concentrated, the crude product was purified by column ($CH_2Cl_2$/MeOH: 100:0-10:1) to obtain the corresponding compound 2-2. $^1H$ NMR (400 MHz, $CDCl_3$) δ=7.64 (dd, J=5.6, 8.8 Hz, 1H), 7.57 (dd, J=2.4, 10 Hz, 1H), 7.03 (m, 1H), 3.71-3.64 (m, 4H), 3.53-3.46 (m, 2H), 2.53-2.44 (m, 4H), 2.10 (s, 3H); MS m/z=305.3[M+H]$^+$.

Step 2: Synthesis of Compound 2-3

Compound 2-2 (1.2 g, 3.94 mmol) was added into concentrated sulfuric acid (10 mL), potassium nitrate (1.20 g, 11.83 mmol) was added at 0° C. The reaction was conducted at 0° C. for 2 hours, and at 50° C. for 16 hours. The reaction liquid was slowly added into an aqueous sodium hydroxide solution (2M) and basified to pH 8, and then extracted with ethyl acetate (20 mL×2). The organic layers were combined, dried over anhydrous sodium sulfate, filtered and concentrated, the crude product was purified by column ($CH_2Cl_2$/MeOH: 100:0-10:1) to obtain the corresponding compound 2-3. $^1H$ NMR (400 MHz, $CDCl_3$) δ=8.40 (d, J=7.2 Hz, 1H), 7.92 (d, J=12 Hz, 1H), 3.74 (s, 2H), 3.71-3.63 (m, 2H), 3.58-3.49 (m, 2H), 2.60-2.40 (m, 4H), 2.12 (s, 3H); MS m/z=350.3 [M+H]$^+$.

Step 3: Synthesis of Compound 2-4

Raney nickel (245.28 mg, 2.86 mmol) was added in anhydrous methanol (5 mL), compound 2-3 (0.05 g, 143.15 μmol) was added, the reaction was conducted at 20° C. for 1 hour in the presence of hydrogen (15 psi). After recovering the catalyst, the reaction liquid was removed by a rotary evaporator to obtain the corresponding compound 2-4. MS m/z=320.2[M+H]$^+$.

Step 4: Synthesis of Compound 2

Compound 1-5 (40 mg, 123.33 μmol) and compound 2-4 (39.38 mg, 123.33 μmol) were added into pyridine (2 mL), T3P in ethyl acetate (784.83 mg, 1.23 mmol, 733.49 μL, 50% content) was added dropwisely. The reaction was conducted at 30° C. for 2 h, directly concentrated, and purified by pre-HPLC (column: Welch Xtimate C18, 150×25 mm×5 μm; mobile phase: [$H_2O$ (0.04% HCl)-ACN]; MeCN: 15%-35%, 8 min) to obtain compound 2. $^1H$ NMR (400 MHz, $d_4$-MeOH) δ=9.49 (s, 1H), 9.33 (s, 1H), 8.80-8.73 (m, 1H), 8.55-8.42 (m, 1H), 8.17 (d, J=8.4 Hz, 1H), 8.05 (d, J=8.0 Hz, 1H), 7.85-7.75 (m, 1H), 7.70-7.62 (m, 1H), 7.52 (s, 1H), 4.13 (s, 3H), 4.10 (s, 3H), 3.99 (s, 2H), 3.93-3.82 (m, 2H), 3.75-3.60 (m, 4H), 2.90-2.50 (m, 4H), 2.13 (s, 3H), MS m/z=626.4[M+H]$^+$.

Example 3

3

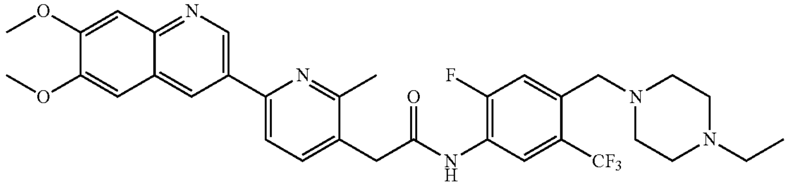

Synthetic Route

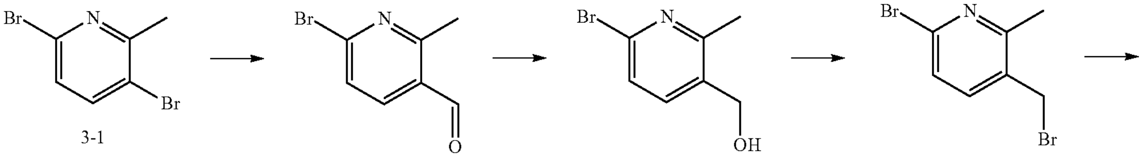

3-1 3-2 3-3 3-4

-continued

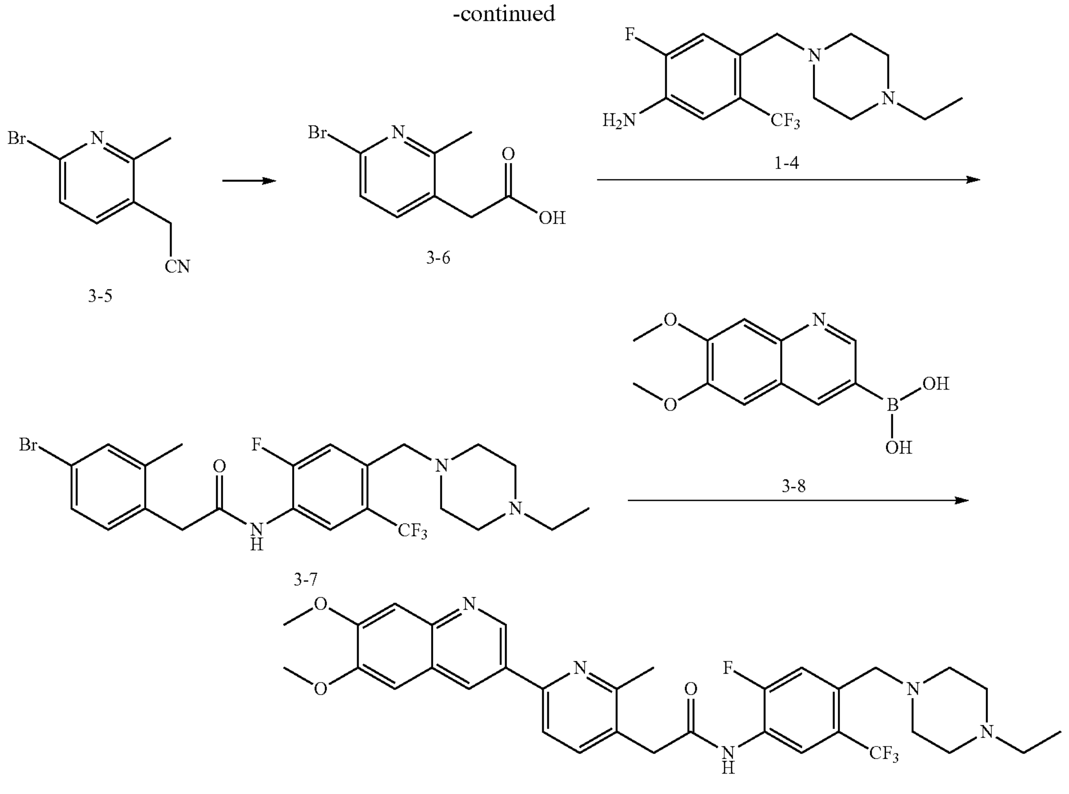

3-5 3-6 3-7

3

Step 1: Synthesis of Compound 3-2

Compound 3-1(24 g, 95.65 mmol, 1 eq) was dissolved in tetrahydrofuran (10 mL), n-butyllithium (2.5M, 40.17 mL, 1.05 eq) was added at −78° C., the reaction was conducted for 1 hour. N,N-dimethylformamide (7.69 g, 105.21 mmol, 8.10 mL, 1.1 eq) was then added and reaction was continued for 1 hour. The reaction mixture was warmed to room temperature, quenched with HCl, and then extracted with ethyl acetate (100 mL×2). The organic layers were combined, washed with an aqueous saturated solution of sodium chloride, dried over anhydrous sodium sulfate, filtered and concentrated to obtain the corresponding compound 3-2. MS m/z=199.8[M+H]+.

Step 2: Synthesis of Compound 3-3

Compound 3-2 (14 g, 69.99 mmol, 1 eq) was dissolved in methanol (30 mL), sodium borohydride (5.56 g, 146.98 mmol, 2.1 eq) was added at 0° C., the reaction was conducted at 20° C. for 2 hours. The reaction liquid was concentrated, water was added, and then the reaction liquid was extracted with ethyl acetate (100 mL×3). The organic layers were combined, washed with an aqueous saturated solution of sodium chloride, and dried over anhydrous sodium sulfate, to obtain crude product. The crude product was purified by column chromatography (petroleum ether: ethyl acetate=10:1) to obtain the corresponding compound 3-3. $^1$H NMR (400 MHz, $CDCl_3$) δ=7.61-7.54 (m, 1H), 7.38-7.27 (m, 1H), 4.70-4.63 (m, 2H), 2.54 (s, 3H); MS m/z=201.8 [M+H]+.

Step 3: Synthesis of Compound 3-4

Compound 3-3 (5.5 g, 27.22 mmol, 1 eq) was dissolved in dichloromethane (12 mL), phosphorus tribromide (8.84 g, 32.67 mmol, 1.2 eq) was added at 0° C., the reaction was conducted at 20° C. for 2 hours. The reaction mixture was quenched with saturated aqueous sodium bicarbonate, and then washed with water (×2). The organic layers were washed with saturated aqueous NaCl, dried over anhydrous sodium sulfate, to obtain crude product. The crude product was purified by column chromatography (petroleum ether: ethyl acetate=10:1) to obtain the corresponding compound 3-4. $^1$H NMR (400 MHz, $d_4$-MeOH) δ=7.66 (d, J=8.0 Hz, 1H), 7.44 (d, J=8.0 Hz, 1H), 4.61 (s, 2H), 2.65 (s, 3H); MS m/z=263.8 [M+H]+.

Step 4: Synthesis of Compound 3-5

Compound 3-4 (5.3 g, 20.00 mmol, 1 eq) was dissolved in ethanol (53 mL), potassium cyanide (2.61 g, 40.01 mmol, 1.71 mL, 2 eq) was added, the reaction was conducted at 60° C. for 5 hours. The reaction mixture was concentrated, water was added, and then the reaction mixture was extracted with dichloromethane (20 mL×2). The organic layers were combined, washed with water (×2), and dried over anhydrous sodium sulfate, to obtain crude product. The crude product was purified by column chromatography (petroleum ether: ethyl acetate=5:1) to obtain the corresponding compound 3-5. $^1$H NMR (400 MHz, $d_4$-MeOH) δ=7.69 (d, J=8.0 Hz, 1H), 7.50 (d, J=8.0 Hz, 1H), 4.01 (s, 2H), 2.60 (s, 3H); MS m/z=210.8 [M+H]+.

Step 5: Synthesis of Compound 3-6

Compound 3-5 (2.4 g, 11.37 mmol, 1 eq) was dissolved in water (3 mL), concentrated sulfuric acid (3 mL) was added, and the reaction was conducted at 100° C. for 5 hours. After adding water, the reaction solution was adjusted with aqueous sodium hydroxide solution to pH 4, and then extracted with ethyl acetate (20 mL×2). The organic layers were combined, washed with saturated aqueous NaCl, dried over anhydrous sodium sulfate, filtered and concentrated, to obtain the corresponding compound 3-6. $^1$H NMR (400 MHz, MeOH-$d_4$) δ=7.53 (d, J=8.0 Hz, 1H), 7.41 (d, J=8.0 Hz, 1H), 3.78 (s, 2H), 2.61 (s, 3H); MS m/r=229.8 $[M+H]^+$.

Step 6: Synthesis of Compound 3-7

Compound 1-4 (1.47 g, 4.80 mmol, 1.1 eq) and compound 3-6 (1 g, 4.37 mmol, 1 eq) were dissolved in pyridine (20 mL), T3P (13.89 g, 21.83 mmol, 12.98 mL, 5 eq) was added, and the reaction was conducted at 20° C. for 2 h. After adding water, the reaction solution was extracted with dichloromethane/methanol (V:V=10:1)(×2). The organic layers were combined, washed with saturated aqueous NaCl, and dried over anhydrous sodium sulfate, to obtain compound 3-7. $^1$H NMR (400 MHz, $d_4$-MeOH) δ=8.36 (d, J=7.3 Hz, 1H), 7.67 (d, J=11.8 Hz, 1H), 7.62-7.52 (m, 1H), 7.50-7.39 (m, 1H), 3.89 (s, 2H), 3.75-3.71 (m, 3H), 3.30-2.54 (m, 11H), 2.53 (s, 3H), 1.29 (t, J=7.4 Hz, 3H); MS m/z=515.8 $[M+H]^+$.

Step 7: Synthesis of Compound 3

Compound 3-8 (90.26 mg, 387.32 μmol, 2 eq), compound 3-7 (0.1 g, 193.66 μmol, 1 eq), and sodium carbonate (61.58 mg, 580.98 μmol, 3 eq) were dissolved in water (3 mL) and dioxane (5 mL), nitrogen was pumped and replaced for three times, Pd(dppf)$Cl_2$ (28.34 mg, 38.73 μmol, 0.2 eq) was added, and the reaction was conducted at 100° C. for 5 h. The solvent was removed by a rotary evaporator, and the residue was extracted with dichloromethane (30 mL×2). The organic layers were combined, washed with saturated aqueous NaCl, dried over anhydrous sodium sulfate, to obtain crude product. The crude product was purified by prep-HPLC (column: Venusil ASB Phenyl, 150×30 mm×5 μm; mobile phase: [$H_2O$ (0.05% HCl)-ACN]; B % (percent gradient of acetonitrile): 20%-50%, 9 min) to obtain compound 3. $^1$H NMR (400 MHz, $d_4$-MeOH) δ=9.63-9.42 (m, 2H), 8.48 (d, J=7.0 Hz, 1H), 8.23-8.09 (m, 2H), 7.81-7.74 (m, 2H), 7.59 (s, 1H), 4.19 (s, 3H), 4.16-4.10 (m, 5H), 3.91 (s, 2H), 3.61 (bs, 2H), 3.29-3.25 (q, J=7.4 Hz, 2H), 3.25-3.15 (m, 4H), 2.82 (s, 3H), 2.69 (bs, 2H), 1.39 (t, J=7.4 Hz, 3H); MS m/z=626.3 $[M+H]^+$.

Example 4

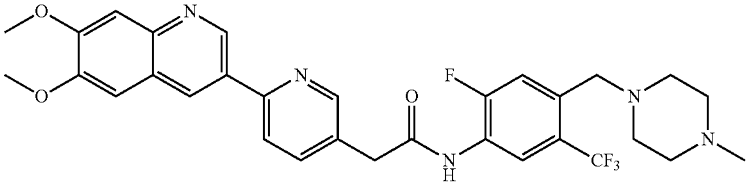

4

Synthetic Route

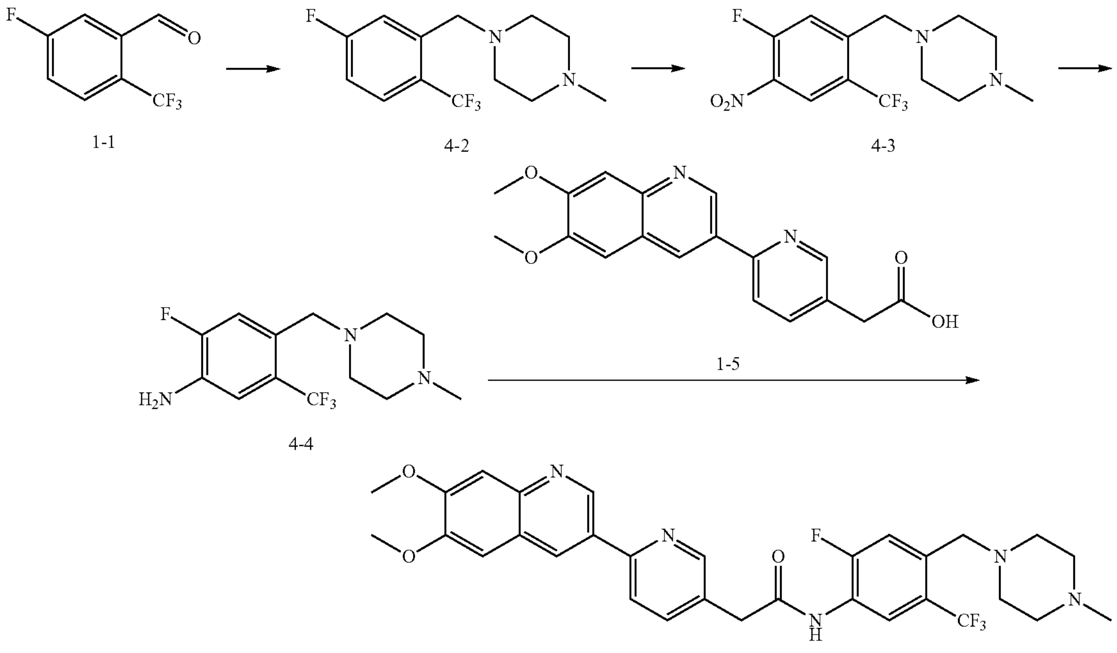

1-1

4-2

4-3

4-4

1-5

4

Step 1: Synthesis of Compound 4-2

Compound 1-1 (0.4 g, 2.08 mmol) and N-methylpiperidine (250.26 mg, 2.50 mmol, 277.14 μL) were added to anhydrous dichloromethane (5 mL), the reaction was conducted at 20° C. for 1 hour. Sodium acetate borohydride (1.32 g, 6.25 mmol) was added and the reaction was conducted at 20° C. for 0.5 hour. The reaction liquid was adjusted with aqueous sodium hydroxide solution (1M) to pH 8, extracted with dichloromethane (5 mL×2). The organic layers were combined, dried over anhydrous sodium sulfate, filtered and concentrated. The crude product was purified by column (100-200 mesh silica gel, mobile phase: dichloromethane and methanol) to obtain the corresponding compound 4-2. $^1$H NMR (400 MHz, $CDCl_3$) δ=7.66-7.62 (m, 1H), 7.44 (dd, J=2.0, 10.0 Hz, 1H), 7.08-7.00 (m, 1H), 3.75 (s, 2H), 3.17-2.79 (m, 8H), 2.68 (s, 3H); MS m/z=277.2 $[M+H]^+$.

Step 2: Synthesis of Compound 4-3

Compound 4-2 (0.1 g, 361.96 μmol, 1 eq) was added into concentrated sulfuric acid(1.95 g, 19.91 mmol, 1.06 mL), then mixed with concentrated nitric acid (114.04 mg, 1.81 mmol, 81.45 μL), and the reaction was conducted at 20° C. for 16 hours. Additional nitric acid (5 eq, 81.45 μL) was added and the reaction was conducted at 50° C. for 9 hours. The reaction liquid was slowly added into water (15 mL), and then extracted with ethyl acetate (10 mL). The aqueous phase was adjusted with aqueous sodium hydroxide solution (1M) to pH 8, extracted with ethyl acetate (20 mL×2). The organic layers were combined, washed with saturated aqueous NaCl (20 mL), dried over anhydrous sodium sulfate, filtered and concentrated, to obtain the corresponding compound 4-3. $^1$H NMR (400 MHz, $CDCl_3$) 5=8.33 (d, J=6.8 Hz, 1H), 7.74 (d, J=12.0 Hz, 1H), 3.73 (s, 2H), 3.02-2.64 (m, 8H), 2.56 (s, 3H); MS m/z=322.1 $[M+H]^+$.

Step 3: Synthesis of Compound 4-4

Raney nickel (1.20 g, 1.40 mmol) was added into methanol (5 mL), compound 4-3 (90 mg, 280.14 μmol) was added, and the reaction was conducted at 20° C. for 0.5 h in the presence of hydrogen (15 psi). The reaction liquid was filtered and concentrated to obtain the corresponding compound 4-4. $^1$H NMR (400 MHz, $CDCl_3$) δ=7.37 (d, J=12.4 Hz, 1H), 7.04 (d, J=8.8 Hz, 1H), 3.84 (s, 2H), 3.55 (s, 2H), 2.72-2.51 (m, 8H), 2.40 (s, 3H); MS m/z=292.1 $[M+H]^+$.

Step 4: Synthesis of Compound 4

Compound 1-5 (80 mg, 246.66 μmol) and compound 4-4 (57.48 mg, 197.33 μmol) were added into pyridine (5 mL), 50% T3P in ethyl acetate (1.57 g, 2.47 mmol, 1.47 mL, 50% content), the reaction was conducted at 30° C. for 1.5 h, directly concentrated. The crude product was washed with an aqueous saturated solution of sodium bicarbonate and adjusted to pH 8-9, extracted with ethyl acetate (10 mL×2). The organic layers were combined, washed with an aqueous saturated solution of sodium chloride (10 mL), dried over anhydrous sodium sulfate, filtered and concentrated, the crude product was purified by pre-HPLC (column: Phenomenex Luna C18, 80×40 mm×3 μm; mobile phase: [$H_2O$ (0.04% HCl)-ACN]; acetonitrile: 13%-38%, 7 min) to obtain compound 4. $^1$H NMR (400 MHz, $d_4$-MeOH) δ=9.56-9.54 (m, 2H), 8.93 (s, 1H), 8.66 (d, J=7.6 Hz, 1H), 8.41 (s, 2H), 8.00 (d, J=11.2 Hz, 1H), 7.80 (s, 1H), 7.60 (s, 1H), 4.35 (s, 2H), 4.18 (s, 3H), 4.15 (s, 2H), 4.12 (s, 3H), 3.94-3.34 (m, 8H), 2.99 (s, 3H); MS m/z=598.3 $[M+H]^+$.

Example 5

5

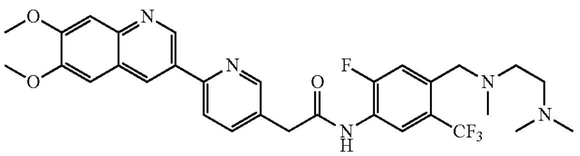

Synthetic Route

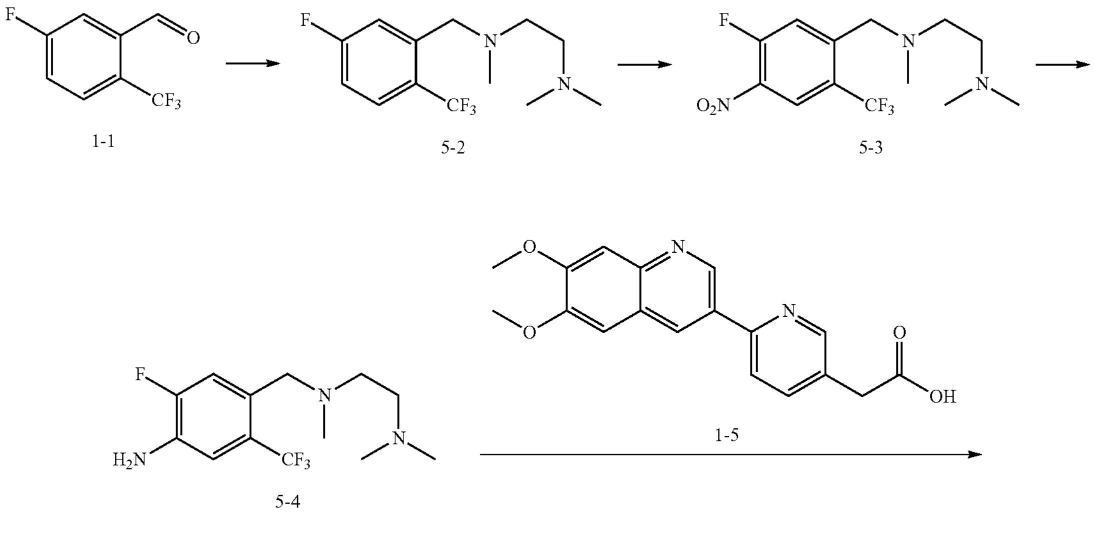

1-1 5-2 5-3 1-5 5-4

-continued

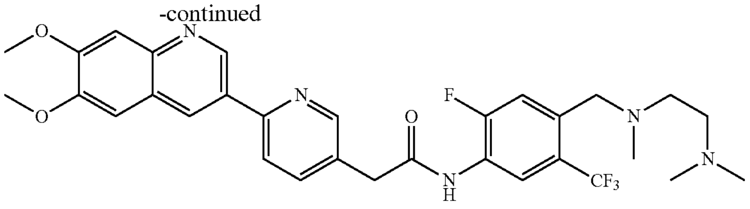

5

Step 1: Synthesis of Compound 5-2

Compound 1-1 (0.5 g, 2.60 mmol) and $N^1$, $N^1$, $N^2$-trimethyldiamine (319.12 mg, 3.12 mmol, 406.01 μL) were added to anhydrous dichloromethane (10 mL), the reaction was conducted at 20° C. for 2 hours. Sodium acetate borohydride (1.65 g, 7.81 mmol) was added and the reaction was conducted at 20° C. for 0.5 hour. The reaction liquid was adjusted with sodium bicarbonate to pH 8, extracted with water (10 mL) and dichloromethane (10 mL). The aqueous phase was continued to be extracted with 10 mL of dichloromethane. The organic layers were combined, dried over anhydrous sodium sulfate, filtered and concentrated. The crude product was purified by column ($CH_2Cl_2$/MeOH: 100:0-10:1) to obtain the corresponding compound 5-2. $^1H$ NMR (400 MHz, $CDCl_3$) δ=7.69-7.52 (m, 2H), 7.07-6.88 (m, 1H), 3.68 (s, 2H), 2.78-2.64 (m, 4H), 2.44 (s, 6H), 2.25 (s, 3H); MS m/z=279.1 $[M+H]^+$.

Step 2: Synthesis of Compound 5-3

Compound 5-2 (0.4 g, 1.44 mmol) was added into concentrated sulfuric acid (7.91 g, 79.05 mmol, 4.30 mL, 98% content), then mixed with concentrated nitric acid (924.16 mg, 14.37 mmol, 660.12 μL, 98%), the reaction was conducted at 50° C. for 5 hours. Saturated aqueous sodium bicarbonate was slowly added into the reaction liquid to adjust pH to 8, and then extracted with ethyl acetate (20 mL×2). The organic layers were combined, washed with saturated aqueous NaCl (30 mL), dried over anhydrous sodium sulfate and filtered (directly used for the next step), to obtain a solution of compound 5-3 in ethyl acetate. MS m/z=324.2 $[M+H]^+$.

Step 3: Synthesis of Compound 5-4

Raney nickel (0.5 g, 10% content) was added into methanol (30 mL), a solution of compound 5-3 (0.25 g, 773.31 μmol) in ethyl acetate (35 mL) was added, and the reaction was conducted at 20° C. for 0.5 h in the presence of hydrogen (15 psi). After recovering the catalyst, the reaction liquid was concentrated to obtain the corresponding compound 5-4. MS m/z=294.2 $[M+H]^+$.

Step 4: Synthesis of Compound 5

Compound 1-5 (0.1 g, 308.33 μmol) and compound 5-4 (72.35 mg, 246.66 μmol) were added into pyridine (2 mL), then 50% T3P in ethyl acetate (1.96 g, 3.08 mmol, 1.83 mL, 50% content) was added, the reaction was conducted at 30° C. for 1.5 h, directly concentrated, and purified by pre-HPLC (column: Welch Xtimate C18, 150×25 mm×5 μm; mobile phase: [$H_2O$ (0.04% HCl)-ACN]; MeCN: 10/6-30%, 8 min) to obtain compound 5. $^1H$ NMR (400 MHz, $d_4$-MeOH) δ=9.56 (d, J=2.0 Hz, 2H), 8.83 (d, J=1.6 Hz, 1H), 8.74 (d, J=7.2 Hz, 1H), 8.27 (d, J=8.0 Hz, 1H), 8.17 (dd, J=2.0, 8.0 Hz, 1H), 8.10 (d, J=11.2 Hz, 1H), 7.77 (s, 1H), 7.56 (s, 1H), 4.58 (s, 2H), 4.16 (s, 3H), 4.11 (s, 3H), 4.06 (s, 2H), 3.75 (s, 4H), 3.00 (s, 6H), 2.81 (s, 3H); MS m/z=600.3 $[M+H]^+$.

Example 6

6

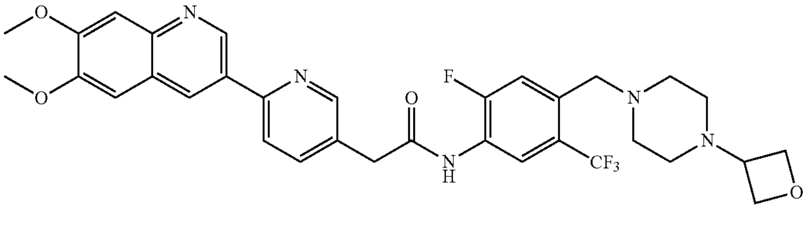

Synthetic Route

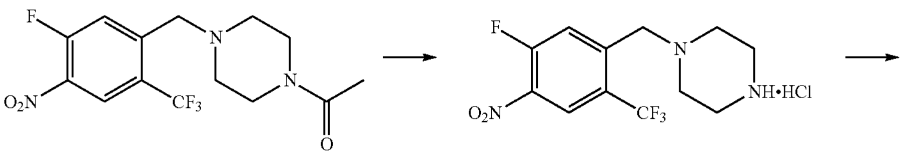

2-3

6-2

-continued

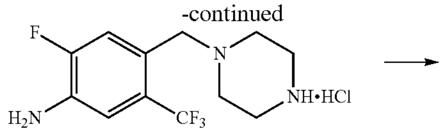

6-3

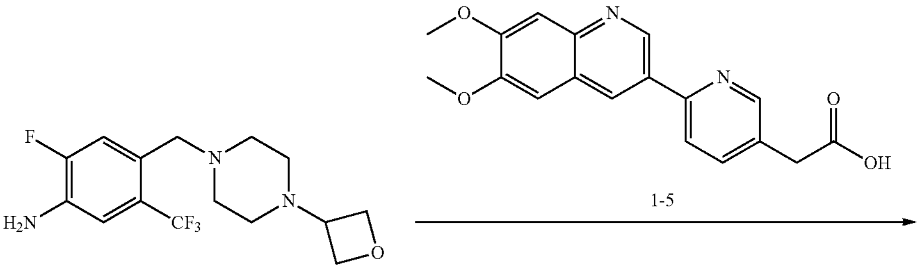

6-4

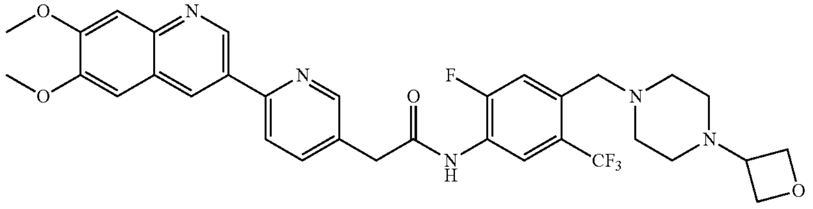

6

Step 1: Synthesis of Compound 6-2

Compound 2-3 (0.6 g, 1.72 mmol) was added to aqueous HCl (2M, 8.59 mL), the reaction was conducted at 100° C. for 1 hour. The reaction liquid was removed by a rotary evaporator. The residue was dissolved in acetonitrile (30 mL×2), concentrated twice by rotary evaporator, to obtain the corresponding compound 6-2. MS m/z=308.2 $[M+H]^+$.

Step 2: Synthesis of Compound 6-3

Raney nickel (1.67 g, 19.53 mmol) was added into methanol (10 mL), compound 6-2 (0.6 g, 1.95 mmol) was added, and the reaction was conducted at 20° C. for 0.5 h in the presence of hydrogen (15 psi). After recovering the catalyst, the solvent was removed by a rotary evaporator to obtain the corresponding compound 6-3. $^1H$ NMR (400 MHz, $d_4$-MeOH) δ=7.33 (d, J=12.4 Hz, 1H), 7.11 (d, J=8.8 Hz, 1H), 3.50 (s, 2H), 2.92-2.87 (m, 4H), 2.52-2.40 (m, 4H); MS m/z=278.1 $[M+H]^+$.

Step 3: Synthesis of Compound 6-4

Compound 6-3 (100 mg, 360.67 μmol, 1 eq) and oxetanone (259.91 mg, 3.61 mmol, 10 eq) were added to anhydrous tetrahydrofuran (5 mL). Sodium acetate borohydride (229.32 mg, 1.08 mmol) was added and the reaction was conducted at 50° C. for 1 hour. The reaction liquid was added into saturated aqueous sodium bicarbonate (15 mL), extracted with ethyl acetate (5 mL×2). The organic layers were combined, washed with saturated aqueous NaCl (10 mL), dried over anhydrous sodium sulfate, filtered and concentrated. The crude product was purified by preparative chromatograph (dichloromethane:methanol=10:1) to obtain the corresponding compound 6-4. MS m/r=334.1 $[M+H]^+$.

Step 4: Synthesis of Compound 6

Compound 1-5 (30 mg, 92.50 μmol) and compound 6-4 (30.83 mg, 92.50 μmol) was added into pyridine (3 mL), 50% T3P in ethyl acetate (588.62 mg, 924.98 μmol, 550.11 μL, 50% content) was added, the reaction was conducted at 30° C. for 1 h, directly concentrated, and purified by pre-HPLC (column: Waters Xbridge BEH C18, 100×25 mm×5 μm; mobile phase: [$H_2O$ (10 mM $NH_4CO_3$)-ACN]; MeCN: 25%-55%, 10 min) to obtain compound 6. $^1H$ NMR (400 MHz, $CDCl_3$) δ=9.33 (d, J=2.0 Hz, 1H), 8.71 (s, 1H), 8.67-8.60 (m, 2H), 7.94-7.82 (m, 2H), 7.63-7.50 (m, 2H), 7.48 (s, 1H), 7.16 (s, 1H), 4.78-4.53 (m, 4H), 4.07 (s, 3H), 4.05 (s, 3H), 3.85 (s, 2H), 3.62 (s, 2H), 3.55-3.48 (m, 1H), 2.63-2.21 (m, 8H); MS r=640.3 $[M+H]^+$.

Example 7

7

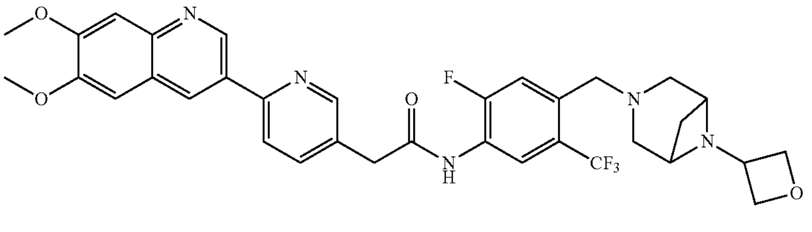

Synthetic Route

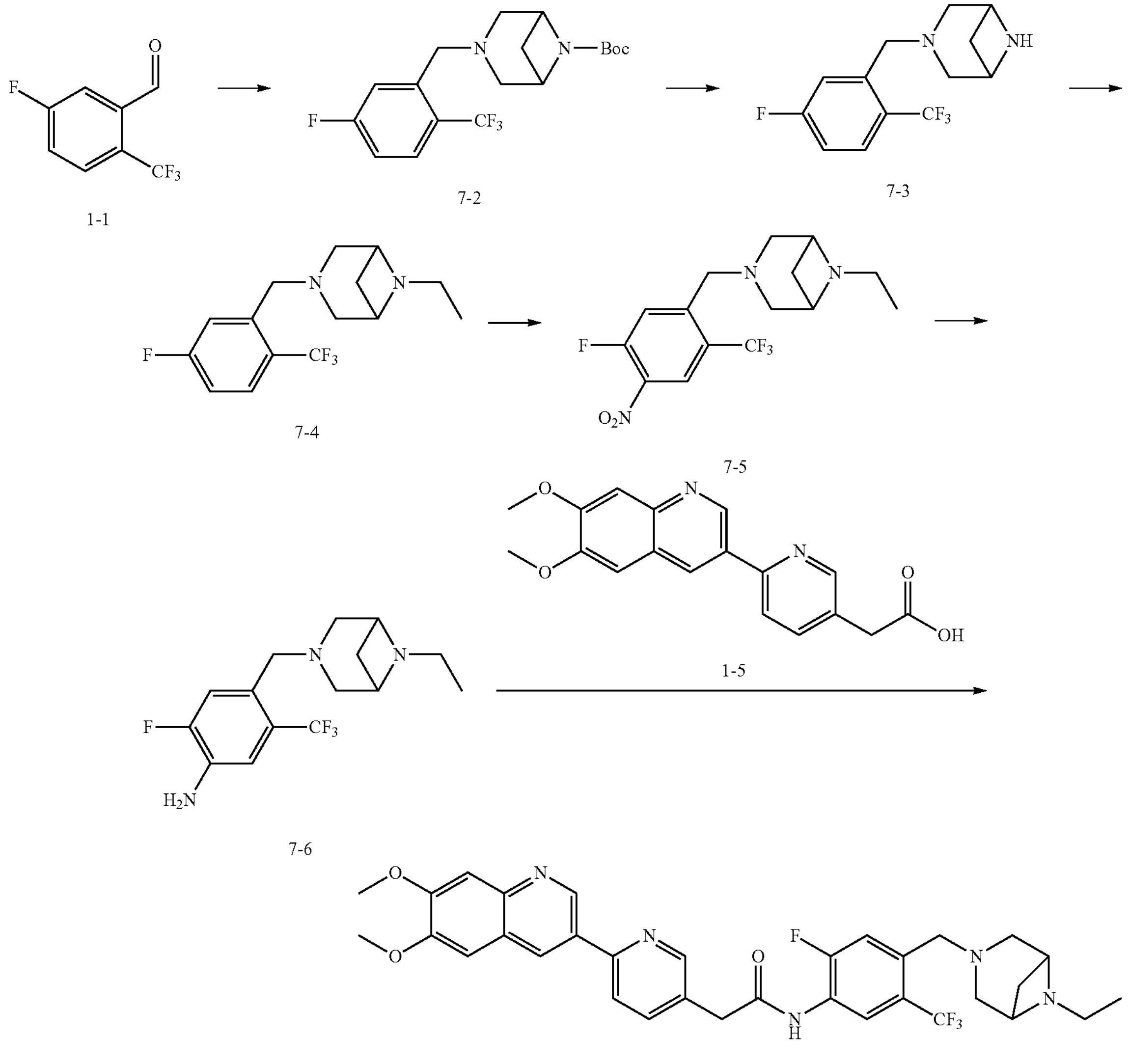

1-1 7-2 7-3 7-4 7-5 1-5 7-6 7

Step 1: Synthesis of Compound 7-2

Compound 1-1 (1 g, 5.21 mmol, 1 eq) and 3,6-diazabicyclo[3.1.1]heptane-6-carboxylic acid tert-butyl ester (1.55 g, 7.81 mmol, 1.5 eq) were dissolved in 1,2-dichloromethane (20 mL), then sodium acetate borohydride (2.21 g, 10.41 mmol, 2 eq) was added, and the reaction was conducted at 15° C. for 0.5 hour. The reaction liquid was extracted with water (25 mL) and dichloromethane (20 mL). The organic layers were dried over anhydrous sodium sulfate and concentrated. The crude product was purified by fast silica column (petroleum ether:ethyl acetate=100:0~3:1) to obtain the corresponding compound 7-2. $^1H$ NMR (400 MHz, $CDCl_3$) δ: 7.63 (dd, J=8.8, 5.2 Hz, 1H), 7.50-7.47 (m, 1H), 7.03-6.98 (m, 1H), 4.14-4.10 (m, 2H), 3.86 (s, 2H), 3.27-3.12 (m, 2H), 2.81 (d, J=9.2 Hz, 2H), 2.45 (dd, J=14.0, 6.0 Hz, 1H), 1.75 (d, J=7.8 Hz, 1H), 1.49 (s, 9H); LCMS m/z=375.3 $[M+H]^+$.

Step 2: Synthesis of Compound 7-3

Compound 7-2 (1 g, 2.67 mmol, 1 eq) was dissolved in ethyl acetate (3 mL), then hydrochloric acid/ethyl acetate (4M, 6.68 mL, 10 eq) was added, the reaction was conducted at 15° C. for 16 hours, and filtered. The filter cake was compound 7-3. $^1H$ NMR (400 MHz, $d_4$-MeOH) S: 7.88-7.83 (m, 2H), 7.34-7.29 (m, 1H), 4.42-4.39 (m, 4H), 3.70-3.48 (m, 4H), 3.00-2.94((m, 1H), 2.55 (d, J=10.4 Hz, 1H); MS m/z=275.2$[M+H]^+$.

Step 3: Synthesis of Compound 7-4

Compound 7-3 (0.4 g, 1.29 mmol, 1 eq, HCl) and acetaldehyde (5M, 514.94 μL, 2 eq) were dissolved in 1,2-dichloroethane (12 mL), sodium acetate borohydride (818.52 mg, 3.86 mmol, 3 eq) was added at 15° C. and then stirred for 1 hour. Water (10 mL) was added ito the reaction liquid, then dichloromethane (10 mL) was added, and the reaction liquid was let stand for liquid separation. The organic layers were dried over anhydrous sodium sulfate and concentrated to obtain the corresponding compound 7-4. $^1H$ NMR (400 MHz, $CDCl_3$) δ: 7.70-7.67 (m, 1H), 7.32 (d, J=9.2 Hz, 1H), 7.10-7.08 (m, 1H), 4.34 (s, 2H), 4.03 (s, 2H), 3.23 (d, J=12.3 Hz, 3H), 3.10 (d, J=12.0 Hz, 2H), 2.91-2.90 (m, 2H), 2.28-2.22 (m, 1H), 1.28-1.22 (m, 3H); MS m/z=303.2 $[M+H]^+$.

Step 4: Synthesis of Compound 7-5

Compound 7-4 (390 mg, 1.29 mmol, 1 eq) was dissolved in sulfuric acid (5 mL), fuming nitric acid (162.58 mg, 2.58 mmol, 116.13 μL, 2 eq) was added, and the reaction was conducted at 60° C. for 20 hours. The reaction liquid was poured into ice water, adjusted with saturated aqueous potassium carbonate (30 mL) to pH 8, and then dichloromethane (40 mL) was added, let stand for liquid separation. The organic layers were dried over anhydrous sodium sulfate and concentrated to obtain compound 7-5. MS m/z=348.2 $[M+H]^+$.

Step 5: Synthesis of Compound 7-6

Compound 7-5 (100 mg, 287.93 μmol, 1 eq) was dissolved in methanol (4 mL), Raney nickel (100.00 mg, 1.17 mmol, 4.05 eq) was added, and the liquid was stirred at 15° C. for 0.5 h in the presence of hydrogen (15 psi). The reaction liquid was filtered. The filter cake was recovered and the filtrate was concentrated, to obtain the corresponding compound 7-6.

Step 6: Synthesis of Compound 7

Compound 7-6 (30 mg, 94.54 μmol, 1 eq) and compound 1-5 (30.66 mg, 94.54 μmol, 1 eq) was dissolved in pyridine (2 mL), 1-propylphosphoric acid cyclic anhydride (601.62 mg, 945.41 μmol, 562.26 μL, 50% content, 10 eq) was added, the reaction mixture was stirred at 35° C. for 0.5 h, directly concentrated, and purified by HPLC (column: Welch Xtimate C18, 150x25 mmx5 μm; mobile phase: [A: MeCN, B: $H_2O$ (0.04% HCl)]; gradient: 5%-20%, 8 min), (column: Phenomenex Gemini-NX C18, 75x30 mmx3 μm; mobile phase: [A: MeCN, B: $H_2O$ (10 mM $NH_4HCO_3$)]; gradient: 30%-50%, 6 min) to obtain compound 7. $^1H$ NMR (400 MHz, $d_4$-MeOH) δ: 9.24 (s, 1H), 8.69 (d, J=10.0 Hz, 2H), 8.40 (s, 1H), 7.97 (d, J=9.6 Hz, 2H), 7.54 (d, J=10.4 Hz, 1H), 7.36 (s, 2H), 4.01-3.91 (m, 10H), 3.65 (s, 2H), 3.01-2.92 (m, 4H), 2.55 (s, 3H), 2.12 (s, 1H), 1.03 (s, 3H); LCMS m/z=624.5 $[M+H]^+$.

Example 8

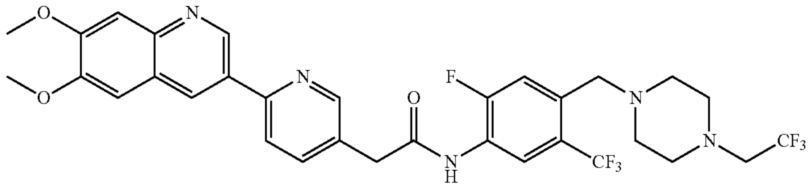

8

Synthetic Route

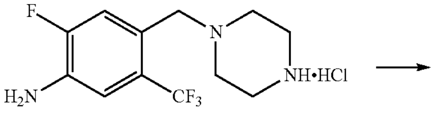

6-3

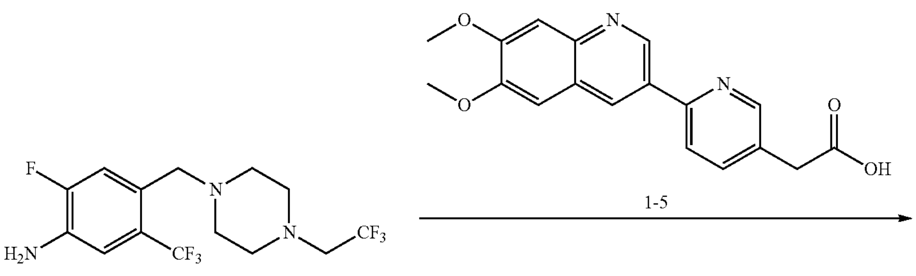

8-2

1-5

-continued

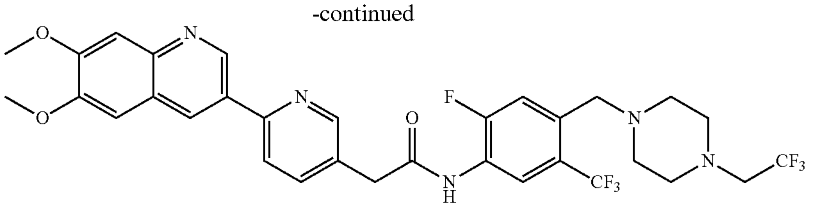

8

Step 1: Synthesis of Compound 8-2

Compound 6-3 (0.1 g, 360.67 μmol) was added into N,N-dimethylformamide (5 mL), cesium carbonate (235.03 mg, 721.34 μmol) and trifluoroethyl trifluoromethanesulfonate (100.45 mg, 432.81 μmol) were added, and the reaction was conducted at 60° C. for 1 hour. The reaction liquid was added into water (10 mL), and then extracted with methyl tert-butyl ether (5 mL×2). The organic layers were combined, washed with an aqueous saturated solution of sodium chloride (5 mL), dried over anhydrous sodium sulfate, filtered and concentrated. The crude material was purified by preparative chromatograph (petroleum ether: ethyl acetate=2.5:1) to obtain the corresponding compound 8-2. MS m/z=360.2 $[M+H]^+$.

Step 2: Synthesis of Compound 8

Compound 1-5 (30 mg, 92.50 μmol, 1 eq) and compound 8-2 (33.23 mg, 92.50 μmol, 1 eq) were added into pyridine (3 mL), 50% T3P in ethyl acetate (588.62 mg, 924.98 μmol, 550.11 μL, 50% content, 10 eq) was added, the reaction was conducted at 30° C. for 2.5 h, directly concentrated, and purified by pre-HPLC (column: Phenomenex luna C18, 80×40 mm×3 μm; mobile phase: [$H_2O$ (0.04% HCl)-ACN]; MeCN: 19%-39%, 7 min) to obtain compound 8. $^1H$ NMR (400 MHz, $d_4$-MeOH) δ=9.60-9.55 (m, 2H), 9.05 (d, J=1.6 Hz, 1H), 8.78 (d, J=7.6 Hz, 1H), 8.65 (dd, J=2.0, 8.4 Hz, 1H), 8.55 (d, J=8.4 Hz, 1H), 8.03 (d, J=11.2 Hz, 1H), 7.86 (s, 1H), 7.67 (s, 1H), 4.56 (s, 2H), 4.27 (s, 2H), 4.22 (s, 3H), 4.15 (s, 3H), 3.55-3.40 (m, 3H), 3.31-3.24 (m, 3H), 3.15-3.00 (m, 4H); MS m/z=666.3 $[M+H]^+$.

Experimental Example 1: In Vitro Inhibitory Activity Evaluation of Human Wild-type and V804M Mutant RET Kinase The inhibitory activity of the test compounds against human wild-type and V804M mutant RET kinase was evaluated by measuring $IC_{50}$ values in a $^{33}$P-labeled kinase activity assay (Reaction Biology Corp).

Buffer conditions: 20 mM hydroxyethyl-piperazine-ethanesulfonic acid (Hepes) (pH 7.5), 10 mM $MgCl_2$, 1 mM ethylene glycol-bis(aminoethyl ether)-tetraacetic acid (EGTA), 0.02% polyoxyethylene lauryl ether (Brij35), 0.02 mg/mL BSA, 0.1 mM $Na_3VO_4$, 2 mM dithiothreitol (DTT), and 1% DMSO.

Compound handling: testing compounds were dissolved in 100% DMSO to specific concentration. Serial dilution can be conducted using Integra Viaflo Assist in DMSO.

Procedures: the substrate was dissolved in freshly prepared Reaction Buffer, the test kinase was added into the substrate solution and gently mixed. Compounds in DMSO were added into the above kinase reaction mixture by Acoustic technology (Echo550) and incubate for 20 minutes at room temperature. The concentrations of the compounds in the reaction solutions were 3 μM, 1 μM, 0.333 μM, 0.111 μM, 0.0370 μM, 0.0123 μM, 4.12 nM, 1.37 nM, 0.457 nM and 0.152 nM. After incubation for 15 min, $^{33}$P-ATP (Specific activity of 0.01 μCi/μL, Km concentration) was added into the reaction mixture to initiate the reaction. The reaction was conducted for 120 minutes at room temperature, and radioactivity was detected by filter-binding method. Kinase activity data can be expressed as the percent remaining kinase activity in test samples compared to vehicle (DMSO only) reactions. IC50 values and curve fits can be obtained using Prism4 (GraphPad Software). Kinase activity data was expressed by comparison between the kinase activity of the group containing text compound and the kinase activity of the blank group (containing only DMSO). The $IC_{50}$ value was obtained by curve fitting with Prism4 software (GraphPad). The experimental results were shown in Table 1.

TABLE 1

| No. | RET(WT)$IC_{50}$(nM) | RET(V804M)$IC_{50}$(nM) |
|---|---|---|
| Compound 1 | 0.5 | 0.9 |

Conclusion: The results of the in vitro enzyme activity test showed that the testing compound possesses an excellent inhibitory action on both wild-type and V804M mutant RET kinases.

Experimental Example 2: Microsome Stability Experimental Purpose

To evaluate the Phase I metabolic stability of the test compound in animal and human liver microsomes.

Experimental Method

10 μL of the test compound working solution and 80 μL of microsome working solution (0.625 mg/mL liver microsome protein) were added to the reaction plate and NCF60 plate, respectively, while only microsome working solution was added to the Blank60 plate, then, the above incubation plates were placed in a 37° C. water bath for pre-incubation for approximately 10 minutes.

After the pre-incubation, 10 μL of a NADPH regeneration system working solution was added into each sample well of all the plates except the NCF60 plate and TO plate to start the reaction, and 10 μL of potassium phosphate buffer was added to each well of the NCF60 plate. The final reaction concentrations of the test sample or control sample were 1 μM, the concentration of the liver microsomes was 0.5 mg/mL.

After incubation for an appropriate time, 300 μL of a stop solution (acetonitrile solution containing 200 ng/mL tolbutamide) was added to each sample well to stop the reaction;

stop solution and then NADPH regeneration system working solution were added to the TO plate in sequence.

All the sample plates were shaken and centrifuged at 3220 rpm for 20 min, and then 100 μL of supernatant was taken from each well and diluted with 300 μL of pure water for LC-MS/MS analysis.

Data Processing

An in vitro elimination rate constant ke of test samples and control samples was obtained by converting a peak area ratio of the sample to the internal standard to remaining percentage(according to the following formula).

% residual amount=(peak area ratio of control to internal standard at any time point/peak area ratio of control to internal standard at 0 min)×100%.

$CL_{int(mic)}$=0.693/$T_{1/2}$/microsome protein (*mg*) *per* milliliter (microsome concentration during incubation)

$CL_{int(liver)}$=$CL_{int(mic)}$×microsome protein (*mg*)/liver weight (*g*)×liver-to-body weight ratio.

Microsome protein (mg)/Liver weight (g): 45 for both animal and human.

Liver-to-body weight ratio: 88 g/kg for mice and 20 g/kg for human.

The experimental results were shown in Table 2.

TABLE 2

| No. | MMS $CL_{int(liver)}$-H (mL/min/kg) | MMS $CL_{int(liver)}$-C (mL/min/kg) | MMS $CL_{int(liver)}$-D (mL/min/kg) | MMS $CL_{int(liver)}$-R (mL/min/kg) | MMS $CL_{int(liver)}$-M (mL/min/kg) |
|---|---|---|---|---|---|
| Compound 1 | 20.7 | 126.7 | 22.5 | <17.3 | 88.5 |

Note:
MMS represents microsome metabolic stability, H represents human, C represents cynomolgus monkey, D represents Beagle, R represents rat, and M represents mice.
Conclusion: The compound of the present disclosure has excellent properties in terms of Phase I metabolic stability.

Experimental Example 3: CYP Inhibition Experimental Purpose

Mixed probe substrate of CYP isozymes were used to evaluate the inhibition of compounds of the present disclosure to human liver microsomal cytochrome P450 isoenzymes (CYP1A2, CYP2C9, CYP2C19, CYP2D6, and CYP3A4).

Experimental Method

The testing compound was dissolved in DMSO to prepare a 10 mM stock solution. 178 μL of the mixture solution of human liver microsomes and substrate was added into non-inhibitor control (NIC) wells and test compound sample wells of the reaction plate, and the reaction plate was placed on ice. 2 μL of blank solvent and test compound working solution was taken from the dilution plate, respectively, and then added into the reaction plate (final concentration: 0.05-50 μM). The reaction plate was preheated in a 37±0.2° C. water bath for 10 minutes. 20 μL of cofactor solution was added into the reaction plate using a liquid handling workstation to initiate the reaction.

After 10 minutes, 400 μL of stop solution was added to the reaction plate to stop the reaction, and the reaction plate was placed on ice for 5 minutes. The plate was shaken for 10 minutes to homogenize the solution, centrifuged at 4000 rpm for 20 minutes, then the supernatant was removed and ultrapure water was added in an appropriate proportion. The peak areas of the substrate and product were detected by liquid chromatography tandem mass spectrometry (LC/MS/MS). Samples were stored at 2-8° C. prior to detection.

Liquid chromatography-tandem mass spectrometry (LC-MS/MS) method was used to determine the ratio of the peak area of the metabolites generated from the probe substrate to the internal standard. Software Analyst (AB Sciex, Framingham, Massachusetts, USA) was used for processing retention time of analyte and internal standard, chromatogram collection, and chromatogram integration.

Data Processing

A nonlinear regression analysis of mean percentage activity of the test compound against concentration was performed using SigmaPlot (V.11). The $IC_{50}$ value was calculated using a three- or four-parameter inverse logarithmic equation. When the percent activity of CYP was greater than 50% under the action of the test compound at the highest concentration (50 μM), $IC_{50}$ values were marked as ">50 μM".

Three-Parameter Logarithmic Equation $$y = \frac{\max}{1 + \left(\frac{x}{IC_{50}}\right)^{-hillslope}}$$

Four-Parameter Inverse Logarithmic Equation $$y = \min + \frac{\max - \min}{1 + \left(\frac{x}{IC_{50}}\right)^{-hillslope}}$$

max: Maximum enzyme activity.

min: Minimal enzymatic activity.

x: Concentration of test compound or positive control inhibitor.

y: Enzyme activity at the corresponding concentration, hillslope: slope.

$IC_{50}$: Half inhibitory concentration.

The 4-parameter inverse logarithmic equation was used when the minimum enzyme activity was within ±10%, otherwise the 3-parameter inverse logarithmic equation was used.

The experimental results were shown in Table 3.

TABLE 3

| No. | CYP1A2_$IC_{50}$_μM | CYP2C9_$IC_{50}$_μM | CYP2C19_$IC_{50}$_μM | CYP2D6_$IC_{50}$_μM | CYP3A4_$IC_{50}$_μM |
|---|---|---|---|---|---|
| Compound 1 | >50 | 12.5 | 16.9 | 18.8 | >50 |

Conclusion: The compound of the present disclosure possesses little inhibitory action on human liver microsomal cytochrome P450 isoenzymes, and has excellent properties in terms of drug interaction and safety.

Experimental Example 4: Pharmacokinetics Study of Mice Experimental Purpose

The purpose of this experiment was to study the pharmacokinetics of the test compound in the plasma of male CD-1 mice after intravenous injection and oral administration.

Experimental Method

The animals were randomly divided into two groups with 2 males in each group. The compounds were formulated into prescribed preparations. Intravenous formulations were formulated with 5% DMSO/95% (6% hydroxypropyl-β-cyclodextrin) to give a clear solution, and oral preparations were formulated with 0.1% Tween80/0.5% HPMC aqueous solution to give a homogeneous suspension.

Whole blood samples were collected from the saphenous vein of the animals 5 minutes, 15 minutes, 30 minutes, 1 hour, 2 hours, 4 hours, 8 hours, 12 hours, and 24 hours after administration. The whole blood sample was added to the centrifuge tube containing anticoagulant, and centrifuged at 3200 g for 10 minutes at 4° C. The supernatant of plasma was taken, frozen quickly on dry ice, and then stored in a −70±10° C. refrigerator until LC-MS/MS analysis.

Data Processing

WinNonlin™ Version 6.3.0 (Pharsight, Mountain View, Calif.) pharmacokinetic software was used to process the plasma drug concentration data of the compounds with a non-compartmental model. The peak concentration (Cmax), peak time (Tmax) and quantifiable end time were obtained directly from the blood drug concentration-time profile.

The following pharmacokinetic parameters were calculated using the log-linear trapezoid method: Plasma clearance rate (CL), volume of distribution (Vd), elimination phase half-life ($T_{1/2}$), average residence time of drug in the body from 0 to the end time point ($MRT_{0-last}$), average residence time of the drug in the body from 0 to infinite time ($MRT_{0-inf}$), area under the time-plasma concentration curve from 0 to the end time point ($AUC_{0-last}$), area under the time-plasma concentration curve from 0 to infinite time ($AUC_{0-inf}$) and bioavailability (F).

The experimental results were shown in Table 4.

TABLE 4

| | | | |
|---|---|---|---|
| Compound 1 | 0.5 mpk intravenous injection | $C_0$(nM) | 1298 |
| | | $T_{1/2}$(hr) | 6.93 |
| | | $Vd_{ss}$(L/kg) | 1.52 |
| | | Cl(mL/min/kg) | 2.68 |
| | | $AUC_{0-inf}$(nM · hr) | 5192 |
| | 2.5 mpk oral administration | $C_{max}$(nM) | 958 |
| | | $T_{max}$(hr) | 8.0 |
| | | $T_{1/2}$(hr) | 5.16 |
| | | $AUC_{0-inf}$(nM · hr) | 12477 |
| | | Bioavailability | 48.9% |

Conclusion: The testing compound possesses an excellent oral bioavailability.

The invention claimed is:

1. A compound of formula (II), or a pharmaceutically acceptable salt thereof, (II)

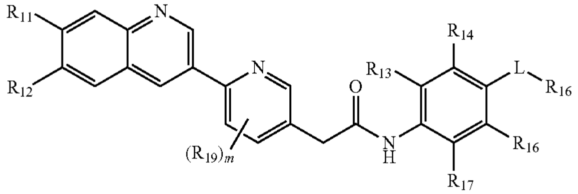

wherein,

L is selected from —$CH_2$—, —$NR_{10}$— and —$CH_2NR_{10}$—;

$R_{10}$ is selected from H and $CH_3$;

$R_{11}$ is —$OCH_3$;

$R_{12}$ is —$OCH_3$;

$R_{13}$ is selected from H, F, Cl, Br, I, OH, $NH_2$, CN and $CH_3$;

$R_{14}$ is selected from H, F, Cl, Br, I, OH, $NH_2$, CN and $C_{1-3}$ alkyl, wherein the $C_{1-3}$ alkyl is optionally substituted by one, two or three Ria;

$R_{16}$ is selected from H, F, Cl, Br, I, OH, $NH_2$, CN and $C_{1-3}$ alkyl, wherein the $C_{1-3}$ alkyl is optionally substituted by one, two or three $R_{1g}$;

$R_{17}$ is selected from H, F, Cl, Br, I, OH, $NH_2$, CN and $CH_3$;

$R_{18}$ is selected from 3,6-diazabicyclo-[3.3.1]heptanyl, piperazinyl, piperidinyl and $C_{1-6}$ alkyl, wherein the 3,6-diazabicyclo-[3.3.1]heptanyl, the piperazinyl, the piperidinyl and the $C_{1-6}$ alkyl are optionally substituted by one, two or three $R_{1h}$;

each $R_{19}$ is independently selected from H, F, Cl, Br, I and $CH_3$, respectively;

m is selected from 0, 1, 2 and 3;

$R_{1d}$ and $R_{1g}$ are independently selected from H, F, Cl, Br, I, OH, $NH_2$, CN and $CH_3$, respectively;

$R_{1h}$ is independently selected from H, F, Cl, Br, I, OH, $NH_2$, CN,

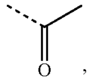
, $C_{1-3}$ alkyl, $C_{1-3}$ alkylamino and oxetanyl, respectively, wherein the

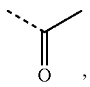
, the $C_{1-3}$ alkyl, the $C_{1-3}$ alkylamino and the oxetanyl are optionally substituted by one, two or three R;

and each R is independently selected from H, F, Cl and I, respectively.

2. The compound or the pharmaceutically acceptable salt thereof according to claim 1, wherein $R_{13}$ is selected from H and F.

3. The compound or the pharmaceutically acceptable salt thereof according to claim 1, wherein $R_{14}$ is selected from H and $CF_3$.

4. The compound or the pharmaceutically acceptable salt thereof according to claim 1, wherein $R_{16}$ is $CF_3$.

5. The compound or the pharmaceutically acceptable salt thereof according to claim 1, wherein $R_{17}$ is H.

6. The compound or the pharmaceutically acceptable salt thereof according to claim 1, wherein $R_{1h}$ is selected from

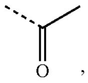 , $CH_3$, $CH_2CH_3$,

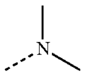 and 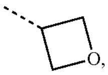, wherein the

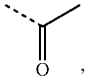 , the $CH_3$, the $CH_2CH_3$, the

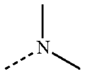

and the

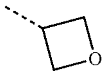

are optionally substituted by one, two or three R.

7. The compound or the pharmaceutically acceptable salt thereof according to claim 6, wherein $R_{1h}$ is selected from

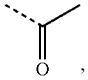 , $CH_3$, $CH_2CH_3$, $CH_2CF_3$,

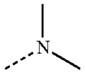 and 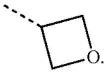.

8. The compound or the pharmaceutically acceptable salt thereof according to claim 1, wherein $R_{1s}$ is selected from $CH_2CH_3$,

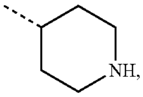 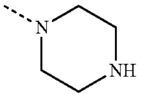 and

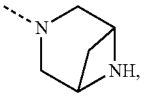

wherein the $CH_2CH_3$, the

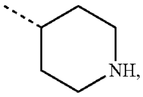

the

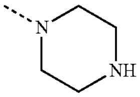

and the

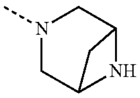

are optionally substituted by one, two or three $R_{1h}$.

9. The compound or the pharmaceutically acceptable salt thereof according to claim 8, wherein $R_{18}$ is selected from

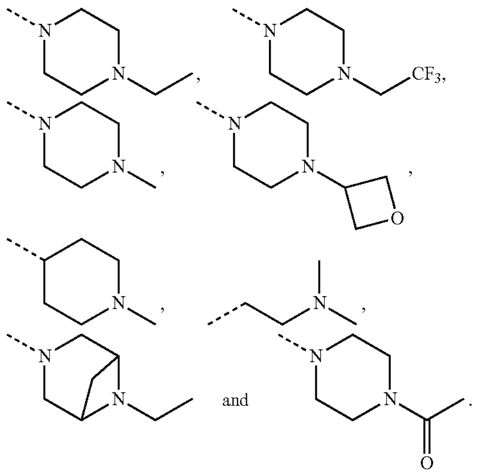

10. The compound or the pharmaceutically acceptable salt thereof according to claim 1, wherein the structural unit

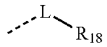
is selected from
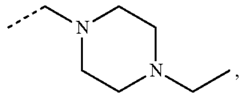
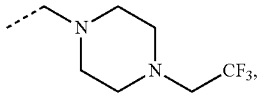
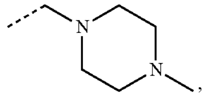
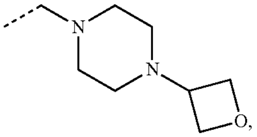
-continued
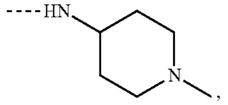
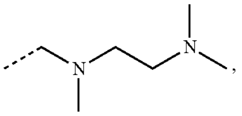
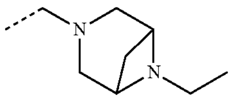
and
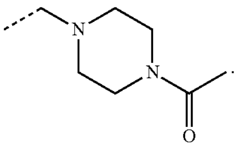
11. The compound or the pharmaceutically acceptable salt thereof according to claim 1, wherein the compound is selected from:
(II-1)
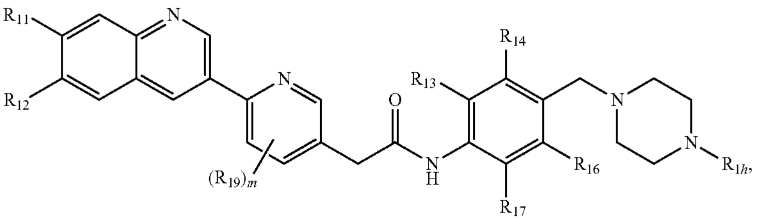
(II-2)
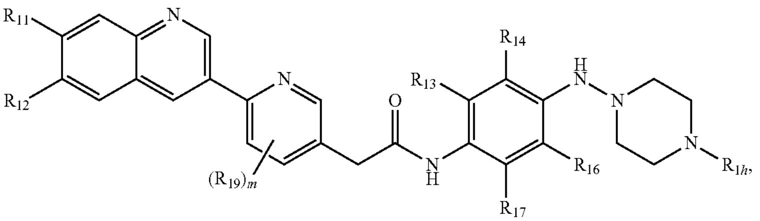
(II-3)
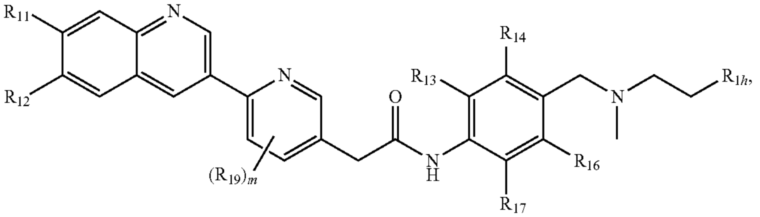
and
(P-1)
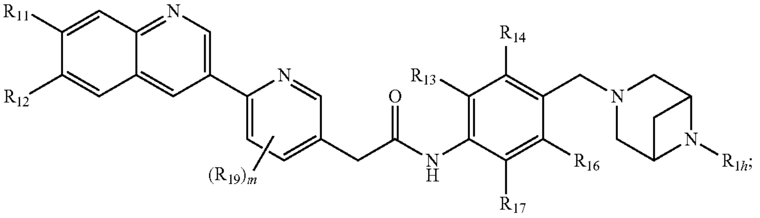

12. The compound or the pharmaceutically acceptable salt thereof according to claim 1 wherein the compound is selected from:
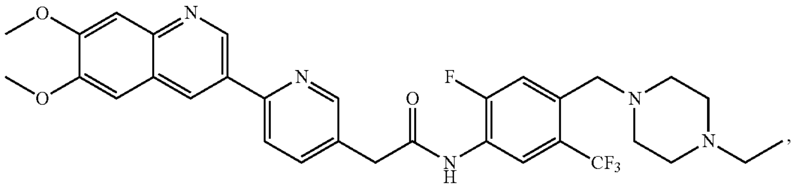
,
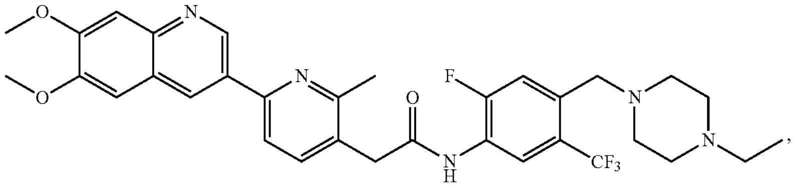
,
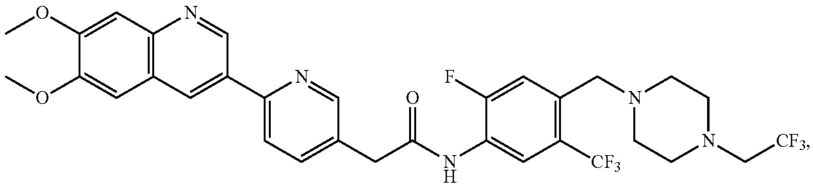
,
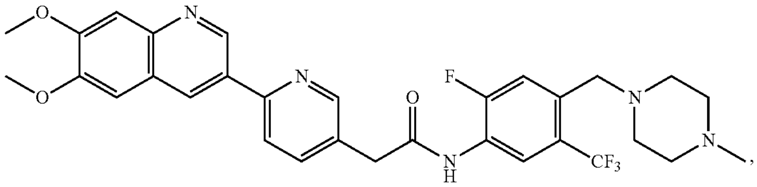
,
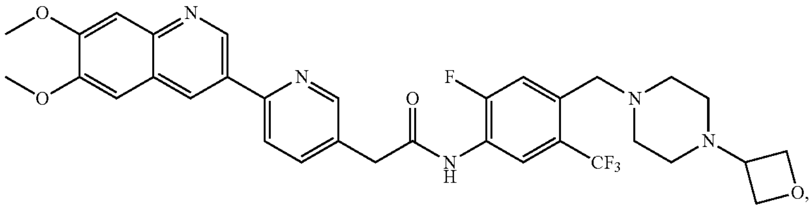
,
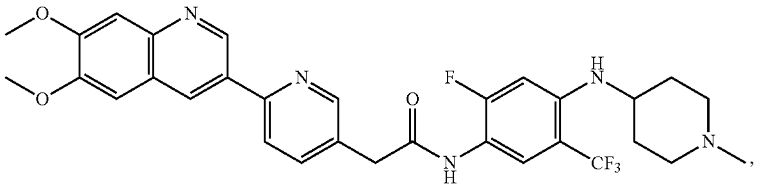
,
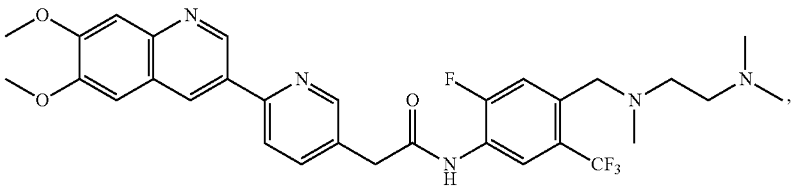
,
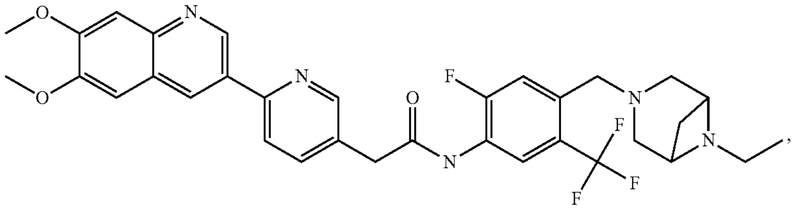
, and -continued

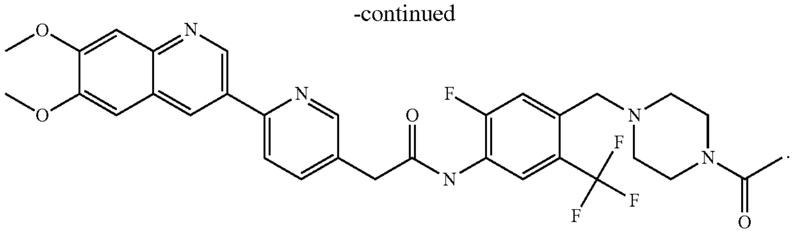

13. A pharmaceutical composition, comprising a therapeutically effective amount of the compound or the pharmaceutically acceptable salt thereof according to claim 1 as an active ingredient, and a pharmaceutically acceptable carrier.

14. A method for treating RET-related disease, comprising administering a therapeutically effective amount of the compound or the pharmaceutically acceptable salt thereof according to claim 1 to a subject in need thereof, wherein the disease is selected from familial thyroid carcinoma, papillary thyroid carcinoma, multiple endocrine neoplasia (MEN2A and 2B), and non-small cell lung cancer.

15. The compound or the pharmaceutically acceptable salt thereof according to claim 6, wherein $R_{1s}$ is selected from $CH_2CH_3$,

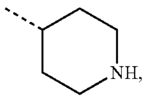 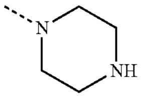 and 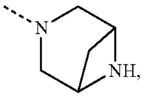

wherein the $CH_2CH_3$, the

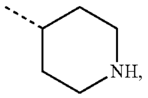

the

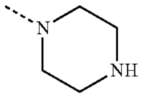

and the

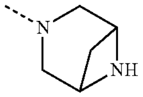

are optionally substituted by one, two or three $R_{1h}$.

16. The compound or the pharmaceutically acceptable salt thereof according to claim 15, wherein $R_{18}$ is selected from

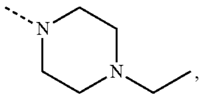 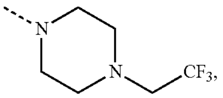

-continued

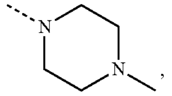 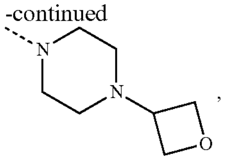

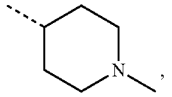 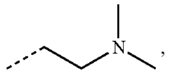

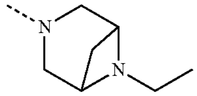 and 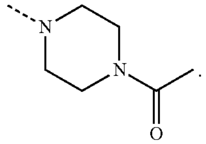

17. The compound or the pharmaceutically acceptable salt thereof according to claim 9, wherein the structural unit

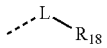

is selected from

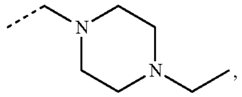 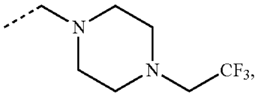

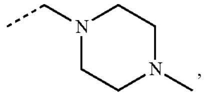 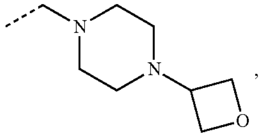

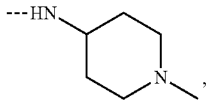 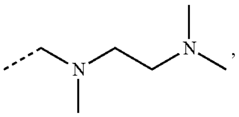

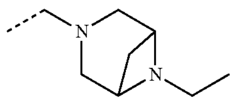 and 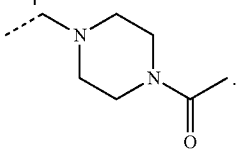

18. The compound or the pharmaceutically acceptable salt thereof according to claim 16, wherein the structural unit

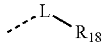

is selected from
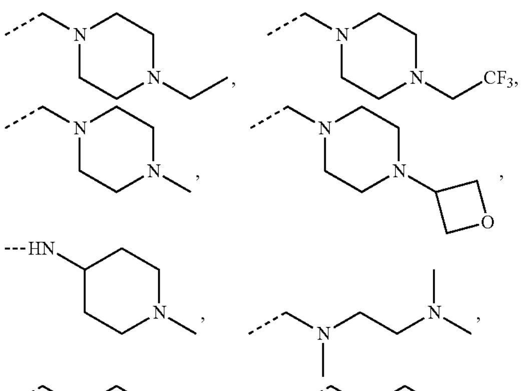
and
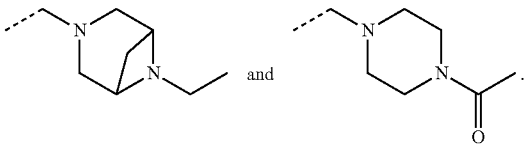
* * * * *